(12) United States Patent
Yoshioka et al.

(10) Patent No.: US 6,720,343 B2
(45) Date of Patent: Apr. 13, 2004

(54) OXADIAZOLE DERIVATIVES HAVING ANTICANCER EFFECTS

(75) Inventors: Takayuki Yoshioka, Osaka (JP); Ryuji Maekawa, Osaka (JP); Fumihiko Watanabe, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 10/257,917

(22) PCT Filed: Apr. 16, 2001

(86) PCT No.: PCT/JP01/03214

§ 371 (c)(1),
(2), (4) Date: Oct. 18, 2002

(87) PCT Pub. No.: WO01/83463

PCT Pub. Date: Nov. 8, 2001

(65) Prior Publication Data

US 2003/0203940 A1 Oct. 30, 2003

(51) Int. Cl.$^7$ ................... A61K 31/4245; C07D 271/06
(52) U.S. Cl. ........................ 514/364; 548/131
(58) Field of Search ............................ 514/364; 548/131

(56) References Cited

U.S. PATENT DOCUMENTS

6,423,729 B1    7/2002    Kurihara

FOREIGN PATENT DOCUMENTS

| EP | 1029541 | 8/2000 |
|---|---|---|
| WO | 00/15213 | 3/2000 |

OTHER PUBLICATIONS

Whittaker et al, *Chemical Reviews*, vol. 99, No. 9, pp. 2735–2776, (1999).
Michaelides et al, *Current Pharmaceutical Design*, vol. 5, pp. 787–819, (1999).
Stearns et al, *Cancer Research*, vol. 53, pp. 878–883, (1993).
Davies et al, *Cancer Research*, vol. 53, pp. 5365–5369, (1993).
Sarén et al, *The Journal of Immunology*, vol. 157, pp. 4159–4165, (1996).
Johnatty et al, *The Journal of Immunology*, vol. 158, pp. 2327–2333, (1997).

*Primary Examiner*—Deborah C. Lambkin
*Assistant Examiner*—Tonya Wright
(74) *Attorney, Agent, or Firm*—Wenderoth, Lind & Ponack, LLP

(57) ABSTRACT

A pharmaceutical composition for treating or preventing cancer containing a compound of the general formula (I), a prodrug, a pharmaceutically acceptable salt, or a solvate thereof as an active ingredient:

$$R^5-\underset{N}{\overset{N-O}{\diagdown\diagup}}-R^4-SO_2-\underset{R^3}{\overset{R^2}{N}}-\underset{COR^1}{\overset{}{\diagdown}}$$ (I)

wherein $R^1$ is hydroxy or the like; $R^2$ is optionally substituted lower alkyl or the like; $R^3$ is hydrogen or the like; $R^4$ is optionally substituted arylene or the like; $R^5$ is optionally substituted aryl or the like.

8 Claims, No Drawings

OXADIAZOLE DERIVATIVES HAVING ANTICANCER EFFECTS

This application is a 371 of PCT/JP01/03214 filed Apr. 16, 2001.

TECHNICAL FIELD

The present invention relates to a pharmaceutical composition containing a sulfonamide derivative having an oxadiazole ring as an active ingredient for treating or preventing cancer.

BACKGROUND ART

An extracellular matrix, consisting of collagen, fibronectin, laminin, proteoglycan, etc., has a function to support tissues, and plays a role in propagation, differentiation, adhesion, or the like in cells. Metalloproteinases which are protease having a metal ion in the active site, especially matrix metalloproteinases (MMP), are concerned with the degradation of the extracellular matrix. Many types of MMP, from MMP-1 to MMP-23, have been reported.

An MMP inhibitor has been developed as an anticancer agent as described in Chem. Rev. 1999, 99, 2735–2776, Current Pharmaceutical Design, 1999, 5, 787–819, etc.

It is described in CANCER RESEARCH 53, 878–883, 1993, CANCER RESEARCH 53, 5365–5369, 1993, etc. that an activity of MMP-2 and MMP-9 is enhanced in cancer patients.

It is well-known that MMP-9 is produced from immune cells such as macrophages and lymphocytes, and its production is controlled by cytokines in The Journal of Immunology 4159–4165, 1996 and The Journal of Immunology 2327–2333, 1997. This MMP-9 is thought to participate when a cell such as macrophage and lymphocyte destroys an extracellular matrix to wander around inflammation or tumor sites. Accordingly, it is supposed that a strong inhibition of MMP-9 may decrease immune response.

A sulfonamide derivative having an oxadiazole ring exhibits an MMP inhibitory activity as described in WO99/04780.

Further, there are other sulfonamide derivatives exhibiting an MMP inhibitory effect.

DISCLOSURE OF INVENTION

As described above, compounds exhibiting an MMP inhibitory activity are under development as an anticancer agent. However, the development of MMP inhibitor having more safety and high efficacy as medicaments has been desired.

In the above situation, the inventors of the present invention have found that certain sulfonamide derivatives having an oxadiazole ring are useful as an anticancer agent with safety and high efficacy.

The present invention relates to:

1) A pharmaceutical composition for treating or preventing cancer containing a compound of the general formula (I), a prodorug, a pharmaceutically acceptable salt, or a solvate thereof as an active ingredient:

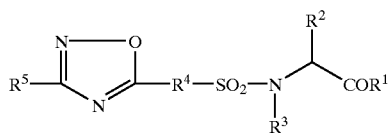

(I)

wherein $R^1$ is NHOH, hydroxy, or lower alkyloxy;

$R^2$ is hydrogen, optionally substituted lower alkyl, optionally substituted aryl, optionally substituted aralkyl, optionally substituted heteroaryl, or optionally substituted heteroarylalkyl;

$R^3$ is hydrogen, optionally substituted lower alkyl, optionally substituted aryl, optionally substituted aralkyl, optionally substituted heteroaryl, or optionally substituted heteroarylalkyl;

$R^4$ is optionally substituted arylene or optionally substituted heteroarylene;

$R^5$ is optionally substituted aryl, optionally substituted heteroaryl, or optionally substituted non-aromatic heterocyclic group.

In more detail, the invention relates to the following 2) to 6).

2) A compound of the formula (I'):

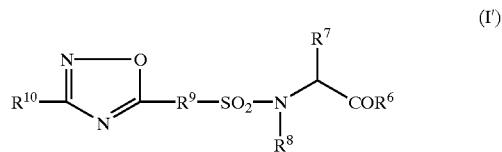

(I')

wherein $R^6$ is NHOH, hydroxy, or lower alkyloxy;

$R^7$ is hydrogen, methyl, isopropyl, isobutyl, benzyl, or indol-3-ylmethyl;

$R^8$ is hydrogen or optionally substituted lower alkyl;

$R^9$ is phenylene or 2,5-thiophene-diyl;

$R^{10}$ is optionally substituted thienyl, optionally substituted furyl, or optionally substituted pyridyl;

a prodorug, or a pharmaceutically acceptable salt, or a solvate thereof.

3) A compound of the following formula:

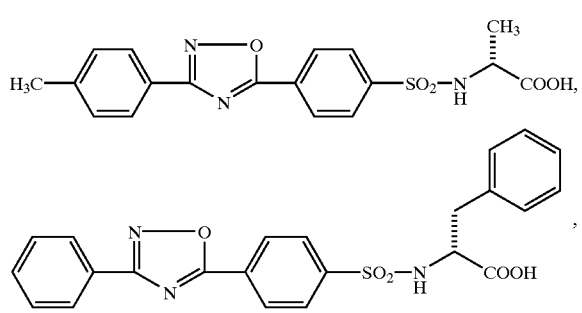

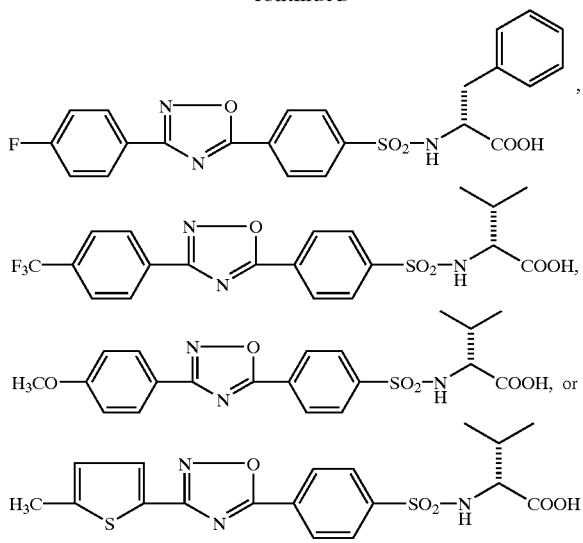

a prodrug, or a pharmaceutically acceptable salt, or a solvate thereof.
4) A parmaceutical composition which contains a compound as described in 2) or 3) as an active ingredient.
5) A parmaceutical composition of 4) as an agent for treating or preventing cancer.
6) A parmaceutical composition of 4) as an agent for preventing metastasis.
7) Use of a compound of 2) or 3) for the preparation of medicine for treating cancer.
8) A method for treating a mammal cancer by administering to a mammal, including human, a therapeutic effective amount of the compound as described in 2) or 3).

In the present specification, the term "lower alkyl" employed alone or in combination with other terms means a straight- or branched chain monovalent hydrocarbon group having 1 to 8 carbon atom(s). Examples of the alkyl include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl and the like. C1 to C6 alkyl is preferred. C1 to C3 alkyl is more preferred.

In the present specification, the term "lower alkenyl" means a straight- or branched chain monovalent hydrocarbon group having 2 to 8 carbon atoms and one or more double bond. Examples of the alkenyl include vinyl, allyl, propenyl, crotonyl, isopentenyl, a variety of butenyl isomers and the like. C2 to C6 alkenyl is preferred. C2 to C4 alkenyl is more preferred.

In the present specification, the term "lower alkynyl" means a straight or branched chain monovalent hydrocarbon group having 2 to 8 carbon atoms and one or more triple bond. The alkynyl may contain (a) double bond(s). Examples of the alkynyl include ethynyl, 2-propynyl, 3-butynyl, 4-pentynyl, 5-hexynyl, 6-heptynyl, 7-octynyl and the like. C2 to C6 alkynyl is preferred. C2 to C4 alkynyl is more preferred.

In the present specification, the term "cycloalkyl" includes cycloalkyl group having 3 to 8 carbon atoms. Examples of cycloalkyl include cyclopropyl, cyclobutyl, cyclopentyl, cyclohexyl, cycloheptyl, cyclooctyl and the like. C3 to C6 cycloalkyl is preferred.

In the present specification, the term "aryl" employed alone or in combination with other terms includes monocyclic or condensed ring aromatic hydrocarbons. Examples include phenyl, 1-naphtyl, 2-naphtyl, anthryl, and the like.

In the present specification, the term "aralkyl" herein used means the above mentioned "lower alkyl" substituted one or more with the above mentioned "aryl" at any possible position. Examples of the aralkyl are benzyl, phenethyl (e.g., 2-phenethyl), phenylpropyl (e.g., 3-phenylpropyl), naphthylmethyl (e.g., 1-naphthylmethyl and 2-naphthylmethyl), anthrylmethyl (e.g., 9-anthrylmethyl), and the like. Benzyl and phenylethy are preferred.

Preferable is benzyl as "aralkyl" for $R^2$ or $R^3$.

In the present specification, the term "heteroaryl" employed alone or in combination with other terms includes a 5 to 6 membered aromatic heterocyclic group which contains one or more hetero atoms selected from the group consisting of oxygen, sulfur, and nitrogen atoms in the ring and may be fused with cycloalkyl, aryl, non-aromatic heterocyclic group, and other heteroaryl at any possible position. Examples of the heteroaryl are pyrrolyl (e.g., 1-pyrrolyl, 2-pyrrolyl, 3-pyrrolyl), furyl (e.g., 2-furyl, 3-furyl), thienyl (e.g., 2-thienyl 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl(e.g., 1H-tetrazolyl), oxadiazolyl (e.g., 1,3,4-oxadiazolyl), thiadiazolyl (e.g., 1,3,4-thiadiazolyl), indolizinyl (e.g., 2-indolizinyl, 6-indolizinyl), isoindolyl (2-isoindolyl), indolyl (e.g., 1-indolyl, 2-indolyl, 3-indolyl), indazolyl (e.g., 3-indazolyl), puriyl (e.g., 8-puriyl), quinolizinyl (e.g., 2-quinolizinyl), isoquinolyl (e.g., 3-isoquinolyl), quinolyl (e.g., 3-quinolyl, 5-quinolyl), phthalazinyl (e.g., 1-phthalazinyl), naphthyridinyl (e.g., 2-naphthyridinyl), quinolanyl (e.g., 2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 3-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzimidazolyl (e.g., 2-benzimidazolyl), benzisoxazolyl (e.g., 3-benzisoxazolyl), benzoxazolyl (e.g., 2-benzoxazolyl), benzoxadiazolyl (e.g., 4-benzoxadiazolyl), benzisothiazolyl (e.g., 3-benzisothiazolyl), benzothiazolyl (e.g., 2-benzothiazolyl), benzofuryl (e.g., 3-benzofuryl), benzothienyl (e.g., 2-benzothienyl) and the like.

Preferable are indolyl and imidazolyl as "heteroaryl" for $R^2$.

Preferable are thienyl, pyridyl, dibenzofuranyl, isoxazolyl, tetrazolyl, and pyrolyl as "heteroaryl" for $R^5$. More preferable is 2-thienyl.

In the present specification, the term "heteroarylalkyl" herein used includes the above mentioned "lower alkyl" substituted one or more with the above mentioned "heteroaryl" at any possible position. Examples of the heteroarylalkyl are thiazolylmethyl (e.g., 4-thiazolylmethyl), thiazolylethyl (e.g., 5-thiazolyl-2-ethyl), benzothiazolylmethyl (e.g., (benzothiazol-2-yl)methyl), indolylmethyl (e.g., indol-3-ylmethyl), imidazolylmethyl (e.g., imidazole-5ylmethyl), benzothiazolylmethyl (e.g., 2-benzothiazolylmethyl), indazolylmethyl (e.g., 1-indazolylmethyl), benzotriazolylmethyl (e.g., 1-benzotriazolylmethyl), benzoquinolylmethyl (e.g., 2-benzoquinolylmethyl), benzimidazolylmethyl (e.g., 2-benzimidazolylmethyl), pyridylmethyl (e.g., 4-pyridylmethyl), and the like.

Preferable are indol-3-ylmethyl and imidazol-5-ylmethyl as "heteroarylalkyl" for $R^2$.

In the present specification, the term "non-aromatic heterocyclic group" employed alone or in combination with other terms includes a 5 to 7 membered non-aromatic ring which contains one or more hetero atoms selected from the group consisting of oxygen, sulfur, and nitrogen atoms in the ring and a condensed ring which are formed with two or more of the non-aromatic ring. Examples of the non-aromatic heterocyclic group are pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidinyl (piperidino, 2-piperidinyl), piperazinyl (e.g., 1-piperazinyl), indolynyl (e.g., 1-indolynyl), isoindolinyl (e.g., isoindolinyl), morpholinyl (e.g., morpholino, 3-morpholinyl), 4H-1,2,4-oxazol-5-one, 1,2,3,4-teterahydro-1,8-naphthyridine, and the like.

Preferable are pyrazolidinyl, piperidinyl, pyrrolinyl, and morpholinyl as "non-aromatic heterocyclic group" for $R^5$.

In the present specification, the term "arylene" herein used means a divalent group of the above-mentioned "aryl". Examples of the arylene are phenylene naphthylene, and the like. Mentioned in more detail, it is exemplified by 1,2-phenylene, 1,3-phenylen, 1,4-phenylene, and the like. Preferable is 1,4-phenylene.

In the present specification, the term "heteroarylene" herein used means a divalent group of the above-mentioned "heteroaryl". Examples of the heteroarylene are thionphene-diyl, furan-diyl, pyridine-diyl, and the like. Mentioned in more detail, it is exemplified by 2,5-thionphene-diyl, 2,5-furan-diyl, and the like. Preferable is 2,5-thionphene-diyl.

In the present specification, the term "lower alkyloxy" herein used are methyloxy, ethyloxy, n-propyloxy, isopropyloxy, n-butyloxy, isobutyloxy, sec-butyloxy, tert-butyloxy, and the like. Preferable are methyloxy, ethyloxy, n-propyloxy, isopropyloxy, and n-butyloxy. More preferable are methyloxy and ethyloxy.

In the present specification, the term "acyl" employed alone or in combination with other terms includes alkylcarbonyl in which alkyl group is the above-mentioned "lower alkyl" and arylcarbonyl in which aryl group is the above-mentioned "aryl". Examples of the acyl are acetyl, propyonyl, benzoyl, and the like. "Lower alkyl" and "aryl" may be substituted respectively with substituents mentioned below.

In the present specification, the term "halogen" herein used means fluoro, chloro, bromo, and iodo. Fluoro, chloro, and bromo are preferred.

In the present specification, the term "lower alkylthio" herein used are methylthio, ethylthio, and the like.

In the present specification, the term "lower alkyloxycarbonyl" herein used are methyloxycarbonyl, ethyloxycarbonyl, n-propyloxycarbonyl, isopropyloxycarbonyl, and the like.

In the present specification, the term "halo(lower)alkyl" employed alone or in combination with other terms includes the above-mentioned "lower alkyl" which is substituted with the above mentioned "halogen" at 1 to 8 positions, preferably, at 1 to 5. Examples of the halo(lower)alkyl are trifluoromethyl, trichloromethyl, difluoroethyl, trifluoroethyl, dichloroethyl, trichloroethyl, and the like. Preferable is trifluoromethyl.

In the present specification, examples of the term "halo (lower)alkyloxy" herein used are trifluoromethyloxy and the like.

In the present specification, examples of the term "lower alkylsulfonyl" herein used are methylsulfonyl, ethylsulfonyl and the like. Preferable is methylsulfonyl.

In the present specification, examples of the term "acyloxy" herein used are acetyloxy, propionyloxy, benzoyloxy and the like.

In the present specification, the term "substituted amino" employed alone or in combination with other terms includes amino substituted with one or two of the above mentioned "lower alkyl", "aralkyl", "heteroarylalkyl" or "acyl". Examples of the optionally substituted amino are methylamino, dimethylamino, ethylmethylamino, diethylamino, benzylamino, acetylamino, benzoylamino and the like. Preferable are methylamino, dimethylamino, ethylmethylamino, diethylamino and acetylamino.

In the present specification, examples of the term "substituted aminocarbonyl" herein used are methylaminocarbonyl, dimethylaminocarbonyl, ethylmethylaminocarbonyl, diethylaminocarbonyl and the like. Preferable is diethylaminocarbonyl.

In the present specification, the substituents of "optionally substituted lower alkyl" are cycloalkyl, hydroxy, lower alkyloxy, mercapto, lower alkylthio, halogen, nitro, cyano, carboxy, lower alkyloxycarbonyl, halo(lower)alkyl, halo (lower)alkyloxy, unsubstituted or substituted amino, unsubstituted or substituted aminocarbonyl, acyl, acyloxy, optionally substituted non-aromatic heterocyclic group, aryloxy (e.g., phenyloxy), aralkyloxy (e.g., benzyloxy), lower alkylsulfonyl, guanidino, azo group, optionally substituted ureide (e.g., ureide, N'-methylureide) and the like. These substituents are able to locate at one or more of any possible positions.

In the present specification, the substituents of "optionally substituted arylene", "optionally substituted heteroarylene", "optionally substituted aryl", "optionally substituted heteroaryl", "optionally substituted non-aromatic heterocyclic group", "optionally substituted aralkyl", "optionally substituted heteroaryl alkyl", "optionally substituted thienyl", "optionally substituted pyridyl", and "optionally substituted furyl" herein used are optionally substituted lower alkyl, cycloalkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, unsubstituted or substituted amino, unsubstituted or substituted aminocarbonyl, acyl, acyloxy, optionally substituted aryl, optionally substituted heteroaryl, optionally substituted non-aromatic heterocyclic group, optionally substituted aralkyl, lower alkylsulfonyl, guanidino group, azo group, or optionally substituted ureide (e.g., ureide, N'-methylureide) and the like. These substituents are able to locate at one or more of any possible positions.

Preferable are unsubstituted ones of "optionally substituted arylene" and "optionally substituted heteroarylene" for $R^4$. These substituents are halogen, nitro, cyano, lower alkyloxy, and the like.

Preferred substituents of "optionally substituted aryl", "optionally substituted heteroaryl", and "optionally substituted non-aromatic heterocyclic group" for $R^5$ are lower alkyl, hydroxy(lower)alkyl, hydroxy, lower alkyloxy, lower alkylthio, halogen, nitro, carboxy, halo(lower)alkyl, halo (lower)alkyloxy, unsubstituted or substituted amino, unsubstituted or substituted aminocarbonyl, and the like. More preferred substituents are halogen and lower alkyl.

Preferable are unsubstituted aryl and substituted aryl with halogen or lower alkyl as "optionally substituted aryl" for $R^5$.

Preferred substituents of "optionally substituted thienyl", "optionally substituted pyridyl", and "optionally substituted furyl" for $R^{10}$ are lower alkyl and halogen.

Preferable are 2-thienyl or 2-thienyl substituted with lower alkyl or halogen at position for $R^{10}$ of the general formula (I').

Preferable is a compound of the general formula (I') wherein $R^6$ is hydroxy, $R^7$ is methyl or isopropyl, $R^8$ is hydrogen, $R^9$ is 2,5-phenylene, $R^{10}$ is hydroxy, non-substituted phenyl, or phenyl substituted with halogen or lower alkyl at 4 position.

BEST MODE FOR CARRYING OUT THE INVENTION

Compounds (I) of the invention are able to be synthesized in accordance with the procedure described in WO97/27174 or as follows.

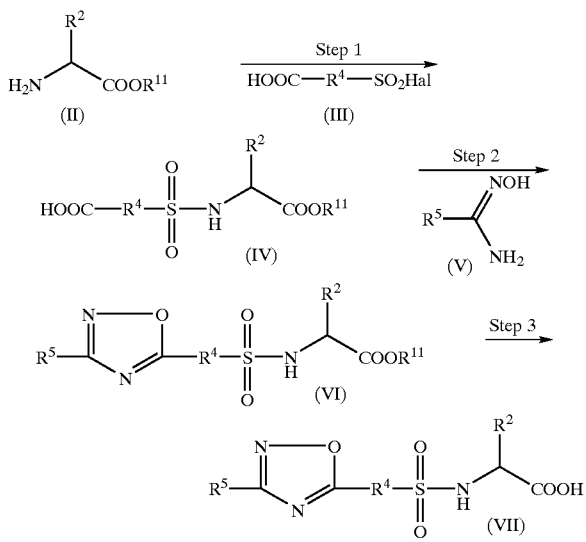

wherein $R^2$, $R^4$, and $R^5$ are as defined above, Hal is halogen, $R^{11}$ is protecting group of carboxy.

(Step 1)

This step is a process of obtaining a sulfonamide derivative (IV) from a compound (II) as a starting material. The process may be carried out in accordance with the same procedure as (Method A-Step 1) in WO97/27174.

(Step 2)

This step is a process of constructing an oxadiazole ring by the reaction of a compound (IV) and a compound (V).

A compound (IV) is dissolved in diglyme and toluene, etc., and then to the reaction mixture are added oxalyl chloride and N,N-dimethylformamide at 0 to 30° C., preferably 0 to 20° C., and then the reaction mixture is stirred preferably for 60 to 120 min. To a solution of a compound (V) and pyridine in diglyme and toluene is added the solution of acyl chloride prepared above under ice-cooling, and then the reaction mixture is stirred at 0 to 110° C. for 2 to 18 h, preferably 2 to 3 h. A compound (VI) is obtained by a usual post-treatment.

(Step 3)

This step is a process of obtaining a compound (VII) by removing the protecting group of carboxyl of a compound (VI). It may be carried out in accordance with a usual method as described in "Protective Groups in Organic Synthesis, Theodora W Green (John Wiley & Sons)" and the like.

The term "the compounds of the present invention" herein used includes a pharmaceutically acceptable salt and a solvate thereof. For example, a salt with an alkali metal (e.g., lithium, sodium, and potassium), an alkaline earth metal (e.g., magnesium and calcium), an ammonium, an organic base, an amino acid, a mineral acid (e.g., hydrochloric acid, hydrobromic acid, phosphoric acid, and sulfuric acid), or an organic acid (e.g., acetic acid, citric acid, maleic acid, fumaric acid, benzenesulfonic acid, and p-toluenesulfonic acid) and a solvate of them with a solvent are examplified. A hydrate is preferable as a solvat. These salts and solvates can be formed by usual methods. A hydrate may coordinate with an arbitrary number of water molecules.

The present invention includes the prodrug of a compound of the present invention. Prodrug is a derivative of the compound of the present invention having a group which can be decomposed chemically or metabolically, and such prodrug is converted to a pharmaceutically active compound of the present invention by means of solvolysis or by placing the compound in vivo under a physiological condition. The selection method and the process method of an appropriate prodrug derivative are described in the literature such as Design of Prodrugs, Elsevier, Amsterdam 1985. When the compounds of the present invention have a carboxyl group, an ester derivative prepared by reacting a basal acid compound with a suitable alcohol or an amide prepared by reacting a basal acid compound with a suitable amine are exemplified as prodrugs. Particularly preferred esters as prodrugs are methyl ester, ethyl ester, n-propyl ester, iso-propyl ester, n-butyl ester, isobutyl ester, tert-butyl ester, morpholinoethyl ester, N,N-diethylglycolamido ester, and the like. When the compounds of the present invention have a hydroxy group, an acyloxy derivative prepared by reacting with a suitable acyl halide or a suitable acid anhydride are exemplified as prodrugs. Particularly preferred acyloxy derivatives as prodrugs are —$OCOC_2H_5$, —$OCO^t$—Bu, —$OCOC_{15}H_{31}$, —$OCO(m-COONa-Ph)$, —$OCOCH_2CH_2COONa$, —$OCOCH(NH_2)CH_3$, and —$OCOCH_2N(CH_3)_2$, and the like. When the compounds of the present invention have an amino group, an amide derivative prepared by reacting with a suitable acid halide or a suitable acid anhydride are exemplified as prodrugs. Particularly preferred amide derivatives as prodrugs are —$NHCO(CH_2)_{20}CH_3$ and —$NHCOCH(NH_2)CH_3$, and the like.

The compound of the present invention is not restricted to any particular isomers but includes all possible isomers and racemic modifications.

The compound of the present invention has a selective MMP-2 inhibitory activity and an antitumor activity as shown in the experimental examples below.

Furthermore, the compound of the present invention has generally a relatively low percentage of binding to protein, high concentration in blood, and no inhibition of P-450 enzyme. Therefore it has good property for using as medicaments.

When the compound of the present invention is administered to a patient for treating cancer, it can be administered by oral administration such as powder, granules, tablets, capsules, pilulae, and liquid medicine, or by parenteral administration such as injections, suppository, percutaneous formulations, insufflation, or the like. An effective amount of the compound of this invention is formulated by being mixed with appropriate medicinal admixture such as excipient, binder, penetrant, disintegrators, lubricant, and the like, if necessary. When parenteral injection is prepared, the compound of this invention and an appropriate carrier are sterilized to prepare it.

An appropriate dosage varies with the conditions of the patients, an administration route, their age, and their body weight. In the case of oral administration to an adult, the dosage can generally be between 0.01–100 mg/kg/day, preferably 0.1–20 mg/kg/day.

The following examples are provided to further illustrate the present invention and are not to be construed as limiting the scope thereof.

In the examples, the following abbreviations are used.
Me: methyl
Et: ethyl
n-Pr: n-propyl
i-Pr: isopropyl
n-Bu: n-butyl
i-Bu: isobutyl
t-Bu: tert-butyl
Ph: phenyl
Bn: benzyl
Indole-3-yl-methyl: Indole-3-yl-methyl
DMSO: dimethylsulfoxide

EXAMPLE

Example 1

Preparation of Compound (A-1)

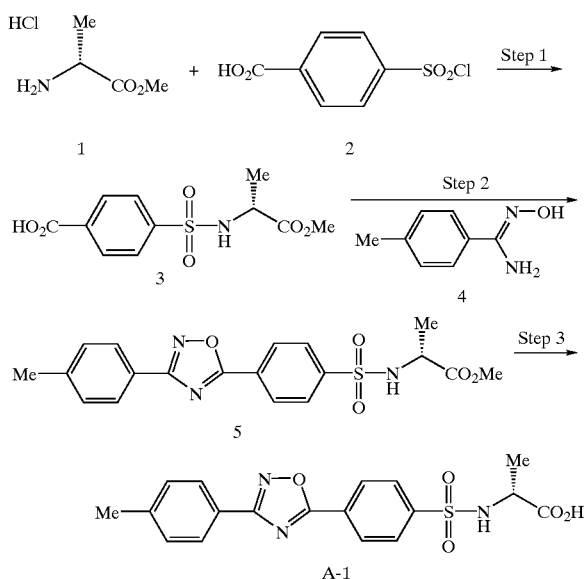

(Step 1)

To a solution of D-valine methyl ester hydrochloride (1) (8.2 g, 40.8 mmol) in water (100 mL) were added sodium carbonate (8.65 g) and acetone (80 mL) under ice-cooling. To the mixture were added water (50 mL) and 4-chlorosufonylbenzoic acid (2) (6 g, 27.2 mmol), and then the reaction mixture was stirred under ice-cooling for 2 h. The reaction mixture was poured into ice-2 mol/L-hydrochloric acid and extracted with ethyl acetate. The organic layer was washed with brine, dried over anhydrous sodium sulfate, and concentrated under reduced pressure. Crystallization of the residue from ethyl acetate (or acetone)/hexane gave compound (3) (6.2 g, 79.3%).

m.p.: 197–199° C.

IR(KBr, ν max cm$^{-1}$) 3500–2500, 3296, 3259, 1739, 1718, 1689, 1344, 1171.

$^1$H NMR (DMSO-d$_6$, δ ppm): 1.88 (d, J=7.2 Hz, 3H), 3.42 (s, 3H), 3.94 (m, 1H), 7.88 (d, J=8.4 Hz, 2H), 8.11 (d, J=8.4 Hz, 2H), 8.52 (d, J=8.7 Hz, 1H), 13.35 (br s, 1H).

$[\alpha]_D$+23.1±1.2 (c=0.507, DMSO, 23° C.).

Analysis for C$_{11}$H$_{13}$NO$_6$S. Calcd.: C, 45.99; H, 4.56; N, 4.88; S, 11.16. Found: C, 45.57; H, 4.40; N, 4.87; S, 11.10.

(Step 2)

To a solution of compound (3) (23.61 g, 82.2 mmol) in diglyme (240 mL) were added oxalyl chloride (8.60 ml, 98.6 mmol) and N,N-dimethylformamide (0.2 mL), and then the reaction mixture was stirred at room temperature for 80 min. To a solution of a compound (4) (12.34 g, 82.2 mmol), pyridine (20 mL, 247 mmol) and diglyme (130 mL) was added the solution of acyl chloride prepared above under ice-cooling, and then the reaction mixture was stirred at room temperature for 1.5 h and at 110° C. for 1 h. The reaction mixture was cooled to 40° C. during 1 h, the supernatant was poured into ice-water (400 mL) and the mixture was stirred for 1 h. The resulting crystal was filtered and washed with water, and then dissolved in ethyl acetate. The organic layer was washed with 2 mol/L hydrochloric acid (100 mL), saturated aqueous sodium hydrogen carbonate solution (100 mL), and brine (100 mL), succesively, dried over anhydrous sodium sulfate, and concentrated under reduced pressure. Crystallization of the residue from ethyl acetate/hexane gave compound (5) (22.64 g, 68.6%).

m.p.: 148–150° C.

IR(KBr, ν max cm$^{-1}$) 3440, 3284, 1743, 1346, 1169, 1133.

$^1$H NMR (CDCl$_3$, δ ppm): 1.43 (d, J=7.2 Hz, 3H), 2.44 (s, 3H), 3.57 (s, 3H), 4.08 (m, 1H), 5.35 (d, J=8.4 Hz, 1H), 7.33 (d, J=8.1 Hz, 2H), 8.03 (d, J=9.0 Hz, 2H), 8.06 (d, J=8.1 Hz, 2H), 8.36 (d, J=9.0 Hz, 2H).

$[\alpha]_D$+17.8±1.2 (c=0.505, DMSO, 24° C.).

Analysis for C$_{19}$H$_{19}$N$_3$O$_5$S. Calcd.: C, 56.84; H, 4.77; N, 10.47; S, 7.99. Found: C, 57.21; H, 4.77; N, 10.61; S, 7.89.

(Step 3)

To a solution of compound (5) (22.64 g, 56.50 mmol) in dimethylsulfoxide (230 mL) was added 1 mol/L aqueous sodium hydroxide solution (141 mL) at room temperature, and then the reaction mixture was stirred for 18 h. The resulting sodium salt was filtered and washed with ethyl acetate (100 mL) The salt was poured into ice-2 mol/L-hydrochloric acid (100 mL) and extracted with ethyl acetate/tetrahydrofuran (10:1, 300 mL, 200 mL). The organic layer was washed with brine (2×200 mL), dried over anhydrous sodium sulfate, and concentrated under reduced pressure. Crystallization of the residue from ethanol/water gave compound (6) (17.70 g, 81.0%).

m.p.: 200–203 ° C.

IR(KBr, ν max cm$^{-1}$) 3240, 1726, 1346, 1151.

$^1$H NMR (DMSO-d$_6$, δ ppm) 1.20 (d, J=7.5 Hz, 3H), 2.41 (s, 3H), 3.87 (m, 1H), 7.43 (d, J=8.1 Hz, 2H), 8.01 (d, J=8.1 Hz, 2H), 8.04 (d, J=8.1 Hz, 2H), 8.36 (d, J=8.1 Hz, 2H), 8.48 (m, 1H), 12.80 (br s, 1H).

$[\alpha]_{365}$−12.2±1.0 (c=0.502, DMSO, 24° C.).

Analysis for C$_{18}$H$_{17}$N$_3$O$_5$S. Calcd.: C, 55.80; H, 4.42; N, 10.85; S, 8.28. Found: C, 55.52; H, 4.46; N, 10.81; S, 8.23.

Example 2

Preparation of Compound (A-2)

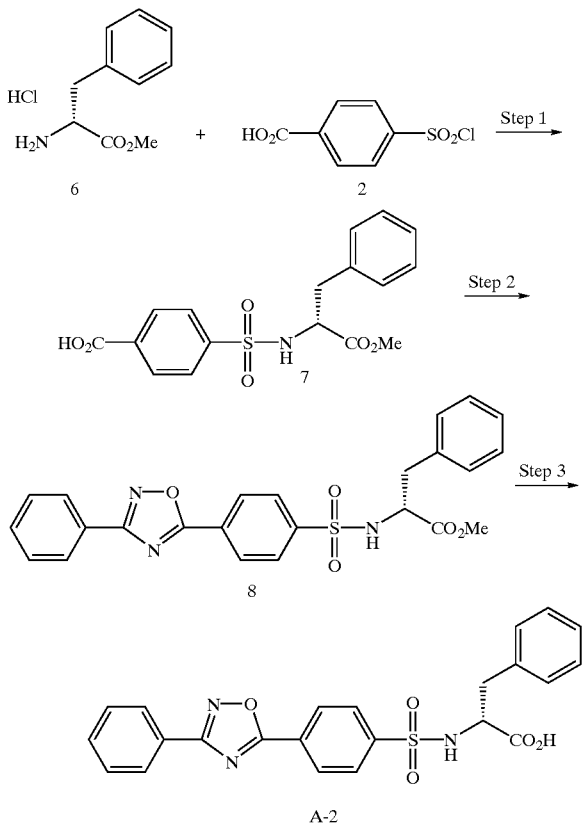

(Step 1)

To a solution of D-valine methyl ester hydrochloride (6) (18.12 g, 84 mmol) in water (100 mL) were added 2M aqueous sodium carbonate solution (61.25 mL) and 4-chlorosufonylbenzoic acid (2) (16.09 g, 70 mmol), under ice-cooling and the reaction mixture was stirred at room temperature for 3 h. The reaction mixture was poured into ice-2 mol/L-hydrochloric acid and extracted with ethyl acetate. The organic layer was washed with brine, dried over anhydrous sodium sulfate, and concentrated under reduced pressure. Crystallization of the residue from acetone/hexane gave compound (7) (21.56 g, 84.8%).

m.p.: 188–189° C.

IR(KBr, ν max cm$^{-1}$) 3280, 2956, 1737, 1691, 1428, 1346, 1284, 1166, 723.

$^1$H NMR (DMSO-d$_6$, δ ppm): 2.77(dd, J=9.3, 13.5 Hz, 1H), 2.94 (dd, J=5.7, 13.5 Hz, 1H), 3.37 (s, 3H), 4.01 (dt, J=6.0, 9.0 Hz, 1H), 7.08–7.23 (ml 5H), 7.66 (d, J=8.4 Hz, 2H), 7.97 (d, J=8.4 Hz, 2H), 8.69 (d, J=9.0 Hz, 1H), 13.38 (br s, 1H).

$[\alpha]_D$+3.2±0.9 (c=0.505, DMSO, 24° C.).

Analysis for C$_{17}$H$_{17}$NO$_6$S. Calcd.: C, 56.19; H, 4.72; N, 3.85; S, 8.82. Found: C, 56.06; H,4.57; N, 3.93; S, 8.75.

(Step 2)

To a solution of compound (7) (20.0 g, 55 mmol) in diglyme (200 mL) were added oxalyl chloride (5.67 ml, 66 mmol) and N,N-dimethylformamide (0.2 mL), and then the reaction mixture was stirred at room temperature for 1 h. To a solution of benzamidoxime (7.49 g, 55 mmol) and diglyme (75 mL) in other reaction vessel was added pyridine (14.1 mL, 165 mmol) under ice-cooling and then a solution of acyl chloride prepared above under ice-cooling, and then the reaction mixture was stirred at same temperature for 1 h and at 110° C. for 2 h. The reaction mixture was cooled to room temperature, the supernatant was poured into ice-water (400 mL) and the mixture was stirred for 20 min. The resulting precipitate was filtered and washed with diethyl ether, and crystallized from acetone/hexane gave compound (8) (16.5 g, 64.9%).

m.p.: 160–161° C.

IR(KBr, ν max cm$^{-1}$) 3338, 1745, 1342, 1169.

$^1$H NMR (CDCl$_3$, δ ppm): 2.99–3.14 (m, 2H), 3.56 (s, 3H), 4.29 (m, 1H), 5.19 (d, J=9.0 Hz, 1H), 7.05–7.09 (m, 2H), 7.23–7.26 (m, 3H), 7.51–7.56 (m, 3H), 7.89 (d, J=8.7 Hz, 2H), 8.16–8.19 (m, 2H), 8.27 (d, J=8.7 Hz, 2H).

$[\alpha]_D$−6.8±0.9° (c=0.509, DMSO, 24° C.).

Analysis for C$_{24}$H$_{21}$N$_3$O$_5$S. Calcd.: C, 62.19; H, 4.57; N, 9.07; S, 6.92. Found: C, 62.02, H, 4.52; N, 8.95; S, 6.96.

(Step 3)

To a solution of compound (7) (4.41 g, 9.51 mmol) in dimethylsulfoxide (85 mL) was added 1 mol/L aqueous sodium hydroxide solution (28.5 mL) at room temperature, and then the reaction mixture was stirred for 24 h. The resulting sodium salt was filtered, poured into ice-2 mol/L-hydrochloric acid (100 mL) and extracted with ethyl acetate/tetrahydrofuran. The organic layer was washed with brine, dried over anhydrous sodium sulfate, and concentrated under reduced pressure. Crystallization of the residue from ethanol/water gave compound (8) (3.80 g, 88.8%).

m.p.: 221–222° C.

IR(KBr, ν max cm$^{-1}$) 3286, 1720, 1350, 1167.

$^1$H NMR (DMSO-d$_6$, δ ppm): 2.74 (dd, J=9.6, 13.6 Hz, 1H), 3.00 (dd, J=5.0, 13.8 Hz, 1H), 4.00 (m, 1H), 7.02–7.22 (m, 5H), 7.56–7.72 (m, 2H), 7.79 (d, J=7.8 Hz, 2H), 8.13 (m, 2H), 8.21 (d, J=8.4 Hz, 2H), 8.63 (d, J=8.4 Hz, 1H), 12.86 (br s, 1H).

$[\alpha]_D$+1.6±0.9° (c=0.502, DMSO, 24.5° C.).

Analysis for C$_{23}$H$_{19}$N$_3$O$_5$S. Calcd.: C, 61.46; H, 4.26; N, 9.35; S, 7.13. Found: C, 61.40; H, 4.15; N, 9.41; S, 7.16.

Example 93

Preparation of Compound (A-93)

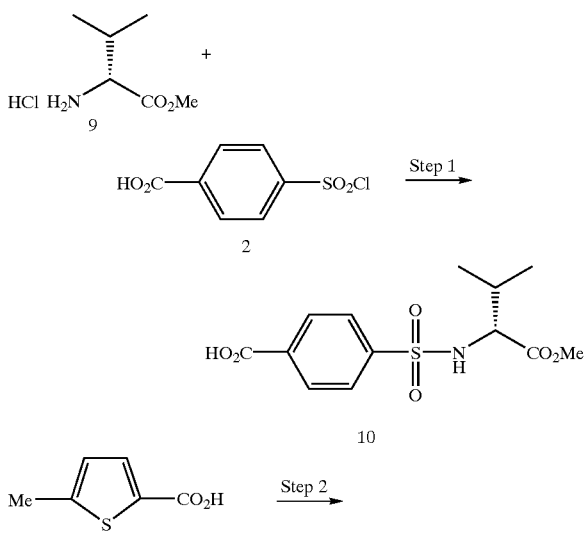

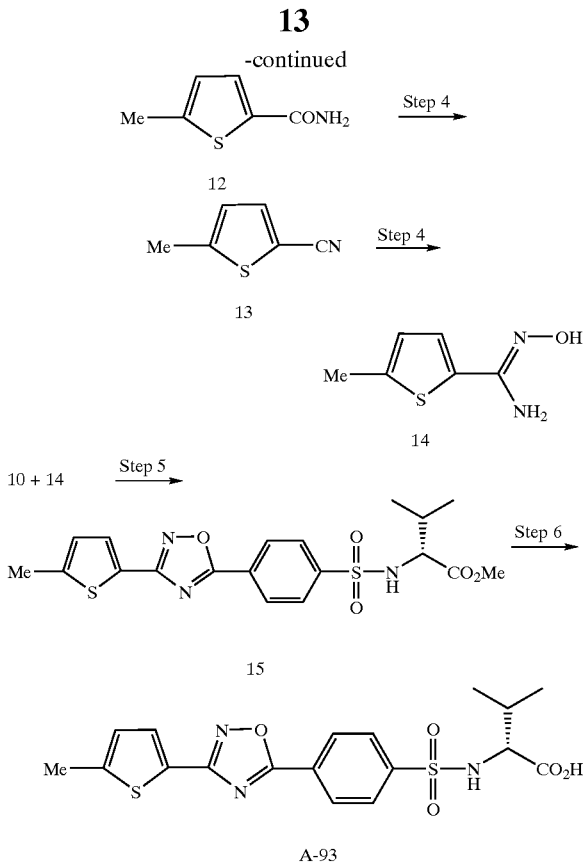

Step 1

To a solution of sodium carbonate (14.4 g, 135.9 mmol) in acetone (100 mL) and water (100 mL) were added D-valine methyl ester hydrochloride (9) (9.1 g, 54.3 mmol) and 4-chlorosufonylbenzoic acid (2) (10.0 g, 45.3 mmol) at room temperature and then the reaction mixture was stirred at room temperature for 1.5 h. The reaction mixture was poured into ice-2 mol/L-hydrochloric acid and extracted with ethyl acetate. The organic layer was washed with brine, dried over anhydrous sodium sulfate, and concentrated under reduced pressure. Crystallization of the residue from ethyl acetate/hexane (1/3) gave compound (10) (9.84 g, 68.8%).

m.p.: 213–215° C.

IR (KBr, ν max cm$^{-1}$) 3268, 2965, 1737, 1691, 1430, 1344, 1284, 1168.

$^1$H NMR (DMSO-d$_6$, δ ppm): 0.80 (t, J=6.6 Hz, 6H), 1.93 (m, 1H), 3.34 (s, 3H), 3.60 (dd, J=7.2, 9.3 Hz, 1H), 7.24–7.89 (m, 2H), 8.06–8.11 (m, 2H), 8.47 (d, J=9.3 Hz, 1H).

[α]$_D$+7.6±1.0 (c=0.502, DMSO, 25° C.).

Analysis for C$_{13}$H$_{17}$NO$_6$S.0.1H$_2$O. Calcd.: C, 49.23; H, 5.47; N, 4.42; S, 10.11. Found: C, 49.17; H, 5.36; N, 4.39; S, 10.30.

(Step 2)

To a solution of 5-methylthiophene-2-carboxylic acid (11) (20.3 g, 143 mmol) in tetrahydrofuran (200 mL) were added N,N-dimethylformamide (0.1 mL) and oxalyl chloride (18.4 mL, 211 mmol) under ice-cooling, and then the reaction mixture was stirred at room temperature for 4 h. The reaction mixture was poured into ice–28% aqueous ammonium hydroxide solution and extracted with ethyl acetate. The organic layer was washed with brine, dried over anhydrous sodium sulfate, and concentrated under reduced pressure. Crystallization of the residue from ethyl acetate/hexane (1/3) gave compound (12) (19.61 g, 97.3%).

m.p.: 162–163° C.

IR (KBr, ν max cm$^{-1}$) 3374, 3170, 1658, 1608, 1469, 1396, 1376.

$^1$H NMR (DMSO-d$_6$, δ ppm): 2.45 (s, 3H), 6.81 (dd, J=1.2, 3.9 Hz, 1H), 7.27 (br s, 1H), 7.53 (d, J=3.9 Hz, 1H), 7.84 (br s, 1H).

Analysis for C$_6$H$_7$NOS. Calcd.: C, 51.04; H, 5.00; N,9.92; S, 22.71. Found: C, 50.93; H, 4.86; N, 9.81; S, 22.67.

(Step 3)

To a suspension of compound (12) (19.0 g, 135 mmol) in toluene (76 mL) was added thionyl chloride (49.0 mL, 675 mmol), and then the reaction mixture was stirred at 100° C. for 7 h. The reaction mixture was poured into ice-saturated aqueous sodium hydrogen carbonate solution and extracted with ethyl acetate. The organic layer was washed with brine, dried over anhydrous sodium sulfate, and concentrated under reduced pressure. The obtained oily compound (13) (22 g) was used at next step without purification.

$^1$H NMR (CDCl$_3$, δ ppm): 2.54 (d, J=0.6 Hz, 3H), 6.78 (m, 1H), 7.44 (d, J=3.3 Hz, 1H).

(Step 4)

A suspension of compound (13) (22 g) and hydroxylammonium chloride (11.3 g, 163 mmol) in ethanol (160 mL) was added triethylamine (22.6 mL, 163 mmol) at room temperature, and then the reaction mixture was stirred at 100° C. for 2 h. The ethanol was removed under reduced pressure, and then to the residue was added water and the mixture was extracted with ethyl acetate. The organic layer was washed with brine, dried over anhydrous sodium sulfate, and concentrated under reduced pressure. Crystallization of the residue from ethyl acetate/hexane (1/3) gave compound (14) (11.32 g, 53.6% in 2 steps).

IR(KBr, ν max cm$^{-1}$) 3390, 3072, 1643, 1585, 1492, 1390, 1371, 931, 808.

$^1$H NMR (DMSO-d$_6$, δ ppm): 2.39 (s, 3H), 5.82 (s, 2H), 6.45 (dt, J=3.3, 0.9 Hz, 1H), 7.24 (d, J=3.3, 1H), 9.52 (s, 1H).

Analysis for C$_6$H$_8$N$_2$OS. Calcd.: C, 46.13; H, 5.16; N, 17.93; S, 20.53. Found: C, 46.09; H, 5.05; N, 17.87; S, 20.69.

(Step 5)

To a suspension of compound (10) (9.80 g, 31.1 mmol) in diglyme (100 mL) were added oxalyl chloride (3.30 mL, 98.6 mmol) and N,N-dimethylformamide (1.0 mL) at room temperature, and then the reaction mixture was stirred 2 h. To a solution of a compound (14) (4.85 g, 31.1 mmol) and pyridine (7.50 mL, 92.7 mmol) and diglyme (50 mL) was added a solution of acyl chloride prepared above under ice-cooling, and then the reaction mixture was stirred at room temperature for 2 h and at 110° C. for 4 h. The reaction mixture was standed at room temperature overnight. The supernatant was poured into ice-water (400 mL) and the resulting crystal was filtered and dissolved in ethyl acetate. The mixture was washed with 2 mol/L hydrochloric acid, saturated aqueous sodium hydrogen carbonate solution, and brine, successively, dried over anhydrous sodium sulfate, and concentrated under reduced pressure. Crystallization of the residue from ethyl acetate/hexane (1/3) gave compound (15) (9.07 g, 67.0%).

m.p.: 155–157° C.

IR (KBr, ν max cm$^{-1}$) 3459, 3280, 1737, 1511, 1365, 1346, 1205, 1170, 1139, 1120, 755

$^1$H NMR (CDCl$_3$, δ ppm): 0.88 (d, J=7.2 Hz, 3H), 0.98 (d, J=6.6 Hz, 3H), 2.08 (m, 1H), 2.58 (d, J=0.9 Hz, 3H), 3.48 (s, 3H), 3.83 (dd, J=4.8, 9.9 Hz, 1H), 5.22 (d, J=9.9 Hz, 1H), 6.85 (dd, J=0.9, 3.6 Hz, 1H), 7.69 (d, J=3.6 Hz, 1H), 8.01 (d, J=8.7 Hz, 2H), 8.32 (d, J=8.7 Hz, 2H).

$[\alpha]_D$+2.8±0.9 (c=0.506, DMSO, 20° C.).

Analysis for $C_{19}H_{21}N_3O_5S$. Calcd.: C, 52.40; H, 4.86; N, 9.65; S, 14.73. Found: C, 52.33; H, 4.73; N, 9.62; S, 14.90.

(Step 6)

A solution of compound (15) (9.0 g, 20.7 mmol) in dimethylsulfoxide (186 mL) was added 1 mol/L aqueous sodium hydroxide solution (62.0 mL) at room temperature, and then the reaction mixture was stirred at 50° C. for 24 h. The reaction mixture was poured into ice-2 mol/L hydrocholic acid was extracted with ethyl acetate. The organic layer was washed with brine, dried over anhydrous sodium sulfate, and concentrated under reduced pressure. Crystallization of the residue from acetone/water gave compound (A-93) (8.4 g, 96.3%).

m.p.: 208–210° C.

IR(KBr, ν max $cm^{-1}$) 3284, 2971, 1712, 1556, 1508, 1403, 1365, 1349, 1253, 1180, 1164, 1145, 1093, 755.

$^1$H NMR (DMSO-$d_6$, δ ppm): 0.82 (d, J=6.9 Hz, 3H), 0.85 (d, J=6.6 Hz, 3H), 1.98 (m, 1H), 2.56 (s, 3H), 3.61 (dd, J=6.6, 7.8 Hz, 1H), 7.02 (m, 1H), 7.72 (dd, J=1.5, 3.6 Hz, 1H), 8.00–8.06 (m, 2H), 8.29–8.25 (m, 2H), 8.37 (d, J=7.8 Hz, 1H), 12.65 (br s, 1H), $[\alpha]_D$-13.4±1.1 (c=0.509, DMSO, 25° C.).

Analysis for $C_{18}H_{19}N_3O_5S_2$. Calcd.: C, 51.29; H, 4.54; N, 9.97; S, 15.22. Found: C, 51.05; H, 4.42; N, 9.92; S, 15.12.

Compounds A-3 to A-92 and A-94 to A-108 described in Table 1 to 15 were synthesized in a manner similar to that described above.

TABLE 1

| Example No. | Compound No. | $R^2$ | $R^5$ | * | $^1$H-NMR(DMSO-$d_6$) |
|---|---|---|---|---|---|
| 3 | A-3 | Bn | Me–(C6H4)– | R | 2.41(s, 3H), 2.74(dd, J=9.6, 13.5 Hz, 1H), 3.97(m, 1H), 7.08–7.12(m, 5H), 7.43(d, J=8.1 Hz, 2H), 7.79(d, J=8.7 Hz, 2H), 8.02(d, J=8.1 Hz, 2H), 8.20(d, J=8.7 Hz, 2H), 8.61(d, J=9.0 Hz, 1H), 12.83(br s, 1H) |
| 4 | A-4 | Me | Cl–(C6H4)– | R | 1.21(d, J=8.6 Hz, 3H), 3.88(m, 1H), 7.70(d, J=8.8 Hz, 2H), 8.05(d, J=8.6 Hz, 2H), 8.13(d, J=8.8 Hz, 2H), 8.37(d, J=8.6 Hz, 2H), 8.48(m, 1H), 12.70(br s, 1H) |
| 5 | A-5 | i-Pr | thiophen-2-yl | R | 0.82(d, J=6.6 Hz, 3H), 0.85(d, J=6.9 Hz, 3H), 1.98(m, 1H), 3.60(dd, J=6.6, 7.5 Hz, 1H), 7.32(dd, J=3.6, 5.1 Hz, 1H), 7.92(dd, J=1.2, 3.6 Hz, 1H), 7.95(dd, J=1.2, 5.1 Hz, 1H), 8.01–8.06(m, 2H), 8.30–8.38(m, 3H), 12.63(br s, 1H) |
| 6 | A-6 | Me | F–(C6H4)– | R | 1.21(d, J=7.5 Hz, 3H), 3.88(m, 1H), 7.81–7.87(m, 2H), 8.02–8.08(m, 4H), 8.34–8.40(m, 2H), 8.47(d, J=8.4 Hz, 1H), 12.67(br s, 1H) |
| 7 | A-7 | Bn | Et–(C6H4)– | R | 1.24(t, J=7.5 Hz, 3H), 2.72(q, J=7.5 Hz, 2H), 2.74(dd, J=9.3, 13.5 Hz, 1H), 2.99(dd, J=5.1, 13.5 Hz, 1H), 3.98(m, 1H), 7.08–7.22(m, 5H), 7.46(d, J=8.1 Hz, 2H), 7.79(d, J=8.4 Hz, 2H), 8.04(d, J=8.4 Hz, 2H), 8.20(d, J=8.1 Hz, 2H), 8.60(d, J=7.8 Hz, 1H), 12.81(br s, 1H) |
| 8 | A-8 | Bn | Me–(C6H4)– | S | 2.41(s, 3H), 2.74(dd, J=9.6, 13.5 Hz, 1H), 2.99(d, J=5.1, 13.5 Hz, 1H), 3.97(m, 1H), 7.08–7.12(m, 5H), 7.43(d, J=8.1 Hz, 2H), 7.79(d, J=8.7 Hz, 2H), 8.02(d, J=8.1 Hz, 2H), 8.20(d, J=8.7 Hz, 2H), 8.61(d, J=9.0 Hz, 1H), 12.83(br s, 1H) |

TABLE 2

| Example No. | Compound No. | R² | R⁵ | * | ¹H-NMR (DMSO-d₆) |
|---|---|---|---|---|---|
| 9 | A-9 | Indol-3-yl methyl | phenyl | R | 2.86(dd, J=9.3, 14.1 Hz, 1H), 3.09 (dd, J=4.2, 14.1 Hz, 1H), 3.95(m, 1H), 6.82–6.91(m, 2H), 7.03–7.12 (m, 2H), 7.31(m, 1H), 7.58–7.70 (m, 5H), 7.98(d, J=8.4 Hz, 2H), 8.10–8.19(m, 2H), 8.53(d, J=6.3 Hz, 1H), 10.73(s, 1H), 12.80(br s, 1 H) |
| 10 | A-10 | Me | phenyl | R | 1.21(d, J=7.2 Hz, 3H), 3.88(m, 1 H), 7.58–7.70(m, 3H), 8.05(d, J=8.7 Hz, 2H), 8.10–8.16(m, 2H), 8.38 (d, J=8.7 Hz, 2H), 8.48(m, 1H), 12.73(br, s, 1H) |
| 11 | A-11 | Bn | 4-Et-phenyl | S | 1.24(t, J=7.8 Hz, 3H), 2.66–2.80(m, 3H), 2.99(dd, J=5.1, 13.5 Hz, 1 H), 3.97(m, 1H), 7.08–7.23(m, 5 H), 7.46(d, J=8.1 Hz, 2H), 7.79 (d, J=8.4 Hz, 2H), 8.04(d, J=8.1 Hz, 2H), 8.20(d, J=8.4 Hz, 2H), 8.58(d, J=8.4 Hz, 1H), 12.82(br s, 1H) |
| 12 | A-12 | i-Pr | 4-F-phenyl | R | 0.82(d, J=6.9 Hz, 3H), 0.85(d, J=6.6 Hz, 3H), 1.98(m, 1H), 3.61 (m, 1H), 7.40–7.50(m, 2H), 8.04 (d, J=8.7 Hz, 2H), 8.10–8.25(m, 2 H), 8.36(d, J=9.0 Hz, 2H), 8.33 (m, 1H), 12.65(br s, 1H) |
| 13 | A-13 | i-Pr | 4-F-phenyl | S | 0.82(d, J=6.6 Hz, 3H), 0.85(d, J=6.6 Hz, 3H), 1.99(m, 1H), 3.61(m, 1 H), 7.47(t, J=9.0 Hz, 2H), 8.04(d, J=8.4 Hz, 2H), 8.18(dd, J=5.4, 9.0 Hz, 2H), 8.36(d, J=8.4 Hz, 2H), 12.65(br s, 1H) |
| 14 | A-14 | i-Pr | 4-Cl-phenyl | R | 0.75–0.95(m, 6H), 1.98(m, 1H), 3.61(m, 1H), 7.70(d, J=8.8 Hz, 2 H), 8.04(d, J=8.8 Hz, 2H), 8.13 (d, J=8.8 Hz, 2H), 8.36(d, J=8.4 Hz, 2H), 8.36(m, 1H), 12.66(br s, 1H) |
| 15 | A-15 | i-Pr | phenyl | R | 0.75–0.95(m, 6H), 1.98(m, 1H), 3.61 (m, 1H), 7.58–7.68(m, 3H), 8.04 (d, J=8.8 Hz, 2H), 8.25(m, 1H), 8.37(d, J=8.4 Hz, 2H), 8.36(m, 1 H), 12.62(br s, 1H) |

TABLE 3

| Example No. | Compound No. | R² | R⁵ | * | ¹H-NMR(DMSO-d₆) |
|---|---|---|---|---|---|
| 16 | A-16 | i-Pr | phenyl | S | 0.82(d, J=6.6 Hz, 3H), 0.85(d, J=6.9 Hz, 3H), 1.98(m, 1H), 3.60 (m, 1H), 7.58–7.69(m, 3H), 8.04 (d, J=7.8 Hz, 2H), 8.09–8.17(m, 2 H), 8.33(br s, 1H), 8.36(d, J=7.8 Hz, 2H), 12.63(br s, 1H) |
| 17 | A-17 | i-Pr | 4-Br-phenyl | R | 0.75–0.95(m, 6H), 1.98(m, 1H), 3.60 (m, 1H), 7.84(d, J=8.4 Hz, 2 H), 8.04(d, J=8.4 Hz, 2H), 8.06 (d, J=8.8 Hz, 2H), 8.36(d, J=8.8 Hz, 2H), 8.36(m, 1H), 12.66(br s, 1H) |
| 18 | A-18 | i-Pr | 4-F₃C-phenyl | R | 0.75–0.95(m, 6H), 1.99(m, 1H), 3.63 (m, 1H), 7.95–8.10(m, 4H), 8.30– 8.50(m, 5H), 8.40(m, 1H), 12.66(br s, 1H) |

TABLE 3-continued

| Example No. | Compound No. | R² | R⁵ | * | ¹H-NMR(DMSO-d₆) |
|---|---|---|---|---|---|
| 19 | A-19 | i-Pr | 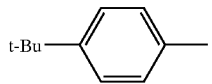 t-Bu—⟨phenyl⟩— | R | 0.82(d, J=6.6 Hz, 3H), 0.85(d, J=6.6 Hz, 3H), 1.34(s, 9H), 1.98(m, 1H), 3.61(t, J=7.2 Hz, 1H), 7.61–7.67(m, 2H), 8.01–8.08(m, 4H), 8.30–8.39(m, 3H), 12.61(br s, 1H) |
| 20 | A-20 | i-Pr | 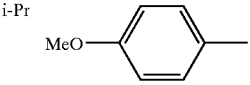 MeO—⟨phenyl⟩— | R | 0.75–0.95(m, 6H), 1.98(m, 1H), 3.56 (m, 1H), 3.86(s, 3H), 7.16(d, J=8.8 Hz, 2H), 8.03(d, J=8.4 Hz, 2H), 8.06(d, J=8.8 Hz, 2H), 8.35 (d, J=8.4 Hz, 2H), 8.35(m, 1H), 12.45(br s, 1H) |
| 21 | A-21 | i-Pr | 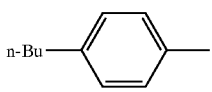 n-Bu—⟨phenyl⟩— | R | 0.75–1.10(m, 9H), 1.20–1.45(m, 2H), 1.50–1.75(m, 2H), 1.98(m, 1H), 2.60–2.75(m, 2H), 3.61(m, 1H), 7.44(d, J=8.2 Hz, 2H), 8.02(d, J=8.4 Hz, 2H), 8.04(d, J=8.4 Hz, 2H), 8.35(d, J=8.4 Hz, 2H), 8.31(m, 1H) |
| 22 | A-22 | i-Pr | 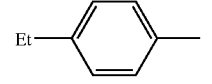 Et—⟨phenyl⟩— | R | 0.82(d, J=6.6 Hz, 3H), 0.85(d, J=6.6 Hz, 3H), 1.24(t, J=7.5 Hz, 3H), 1.98 (m, 1H), 2.71(q, J=7.5 Hz, 2H), 3.61 (dd, J=5.4, 8.4 Hz, 1H), 7.46(d, J=8.4 Hz, 2H), 8.01–8.07(m, 4H), 8.32–8.38 (m, 3H), 12.63(br s, 1H) |
| 23 | A-23 | i-Pr | 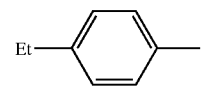 Et—⟨phenyl⟩— | S | 0.82(d, J=6.6 Hz, 3H), 0.85(d, J=6.6 Hz, 3H), 1.24(t, J=7.5 Hz, 3H), 1.78 (m, 1H), 2.72(q, J=7.5 Hz, 2H), 3.61 (m, 1H), 7.46(d, J=8.1 Hz, 2H), 8.04 (d, J=8.7 Hz, 4H), 8.33(br s, 1H), 8.35 (d, J=8.1 Hz, 2H), 12.65(br s, 1H) |

TABLE 4

| Example No. | Compound No. | R² | R⁵ | * | ¹H-NMR (DMSO-d₆) |
|---|---|---|---|---|---|
| 24 | A-24 | i-Pr | 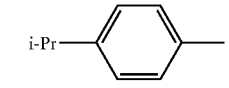 i-Pr—⟨phenyl⟩— | R | 0.83(d, J=6.9 Hz, 3H), 0.86(d, J=7.2 Hz, 3H), 1.26(d, J=6.9 Hz, 6H), 1.98 (m, 1H), 3.01(m, 1H), 3.61(dd, J=6.6, 8.1 Hz, 1H), 7.50(d, J=7.8 Hz, 2H), 8.05(d, J=8.1 Hz, 4H), 8.30–8.39(m, 3H), 12.63(br s, 1H) |
| 25 | A-25 | i-Pr | 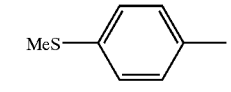 MeS—⟨phenyl⟩— | R | 0.82(d, J=6.9 Hz, 3H), 0.85(d, J=6.9 Hz, 3H), 1.99(m, 1H), 2.56(s, 3H), 3.61(dd, J=6.0, 8.1 Hz, 1H), 7.47(d, J=8.7 Hz, 2H), 8.03(d, J=8.7 Hz, 2H), 8.04(d, J=8.4 Hz, 2H), 8.29–8.38(m, 3H), 12.62(br s, 1H) |
| 26 | A-26 | i-Pr | 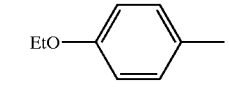 EtO—⟨phenyl⟩— | R | 0.82(d, J=6.6 Hz, 3H), 0.85(d, J=6.6 Hz, 3H), 1.37(t, J=7.2 Hz, 3H), 1.98 (m, 1H), 3.61(dd, J=5.7, 8.4 Hz, 1H), 4.14(q, J=7.2 Hz, 2H), 7.10–7.17(m, 2H), 8.00–8.06(m, 4H), 8.28–8.37(m, 3H), 12.62(br s, 1H) |
| 27 | A-27 | i-Pr | 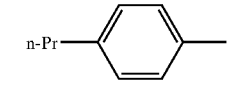 n-Pr—⟨phenyl⟩— | R | 0.82(d, J=6.6 Hz, 3H), 0.85(d, J=6.8 Hz, 3H), 0.92(t, J=7.0 Hz, 3H), 1.50–1.80(m, 2H), 1.98(m, 1H), 2.66(t, J=7.0 Hz, 2H), 3.61(m, 1H), 7.44(d, J=8.2 Hz, 2H), 8.03(d, J=8.4 Hz, 2H), 8.04(d, J=8.8, 2H), 8.36(d, J=8.8 Hz, 2H), 12.70(br s, 1H) |

TABLE 4-continued

| Example No. | Compound No. | R² | R⁵ | * | ¹H-NMR (DMSO-d₆) |
|---|---|---|---|---|---|
| 28 | A-28 | i-Pr | 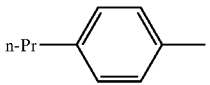 n-Pr— | S | 0.82(d, J=6.9 Hz, 3H), 0.85(d, J=6.9 Hz, 3H), 0.92(t, J=7.5 Hz, 3H), 1.56–1.74(m, 2H), 1.97(m, 1H), 2.66(t, J=7.5 Hz, 2H), 3.60(m, 1H), 7.44(d, J=8.1 Hz, 2H), 8.03(d, J=8.1 Hz, 4H), 8.04(d, J=8.4 Hz, 2H), 8.36(d, J=8.1 Hz, 2H), 12.66(br s, 1H) |
| 29 | A-29 | i-Pr | 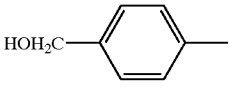 HOH₂C— | R | 0.82(d, J=6.9 Hz, 3H), 0.85(d, J=6.6 Hz, 3H), 1.99(m, 1H), 3.61(m, 1H), 4.62(s, 2H), 5.40(br s, 1H), 7.56(d, J=8.1 Hz, 2H), 8.04(d, J=8.7 Hz, 2H), 8.08(d, J=8.1 hz, 2H), 8.31–8.42(m, 3H), 12.69(br s, 1H) |
| 30 | A-30 | Bn | 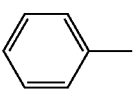 | R | 2.75(dd, J=9.6, 13.5 Hz, 1H), 2.99 (dd, J=5.4, 13.5 Hz, 1H), 3.98(m, 1H), 7.08–7.22(m, 5H), 7.59–7.68(m, 3H), 7.80(d, J=8.7 Hz, 2H), 8.10–8.16 (m, 2H), 8.21(d, J=8.7 Hz, 2H), 8.60 (d, J=7.5 Hz, 1H), 12.81(br s, 1H) |

TABLE 5

| Example No. | Compound No. | R² | R⁵ | * | ¹H-NMR (DMSO-d₆) |
|---|---|---|---|---|---|
| 31 | A-31 | Bn | 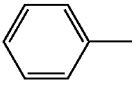 | S | 2.75(dd, J=9.6, 13.5 Hz, 1H), 2.99(dd, J=5.4, 13.5 Hz, 1H), 3.98(m, 1H), 7.08–7.22(m, 5H), 7.59–7.68(m, 3H), 7.80(d, J=8.7 Hz, 2H), 8.10–8.16(m, 2H), 8.21(d, J=8.7 Hz, 2H), 8.60(d, J=7.5 Hz, 1H), 12.82(br s, 1H) |
| 32 | A-32 | Bn | 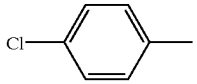 Cl— | R | 2.74(dd, J=9.3, 13.8 Hz, 1H), 2.99(dd, J=5.1, 13.8 Hz, 1H), 3.95(m, 1H), 7.08–7.22(m, 5H), 7.71(d, J=8.7 Hz, 2H), 7.79(d, J=8.7 Hz, 2H), 8.14(d, J=8.7 Hz, 2H), 8.21(d, J=8.7 Hz, 2H), 8.58(m, 1H), 12.77(br s, 1H). |
| 33 | A-33 | Bn | 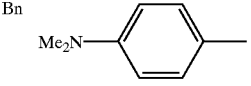 Me₂N— | R | 2.76(dd, J=9.6, 13.5 Hz, 1H), 2.99(dd, J=5.1, 13.5 Hz, 1H), 3.97(m, 1H), 6.86(d, J=8.7 Hz, 2H), 7.08–7.22(m, 5H), 7.78(d, J=8.7 Hz, 2H), 7.91(d, J=8.7 Hz, 2H), 8.18(d, J=8.7 Hz, 2H), 8.58(d, J=7.5 Hz, 1H), 12.80(br s, 1H). |
| 34 | A-34 | Bn | 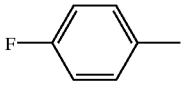 F— | R | 2.75(dd, J=9.6, 13.8 Hz, 1H), 2.99(dd, J=5.4, 13.8 Hz, 1H), 3.98(dt, J=5.1, 9.0 Hz, 1H), 7.09–7.22(m, 5H), 7.42–7.51(m, 2H), 7.76–7.82(m, 2H), 8.14–8.23(m, 4H), 8.61(d, J=9.0 Hz, 1H), 12.81(br s, 1H) |
| 35 | A-35 | Bn | 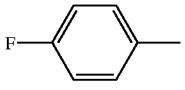 F— | S | 2.74(dd, J=9.6, 13.2 Hz, 1H), 2.99 (dd, J=4.8, 13.2 Hz, 1H), 3.97(m, 1H), 7.09–7.12(m, 5H), 7.47(t, J=9.0 Hz, 2H), 7.79(d, J=9.0 Hz, 2H), 8.14–8.25(m, 4H), 8.61(d, J=8.1 Hz, 1H), 12.84(br s, 1H) |
| 36 | A-36 | Bn | 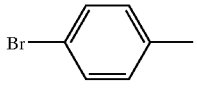 Br— | R | 2.75(dd, J=9.6, 13.5 Hz, 1H), 2.99(dd, J=5.1, 13.5 Hz, 1H), 3.97(m, 1H), 7.08–7.22(m, 5H), 7.79(d, J=8.1 Hz, 2H), 7.84(d, J=8.4 Hz, 2H), 8.06 (d, J=8.1 Hz, 2H), 8.20(d, J=8.4 Hz, 2H), 8.60(m, 1H), 12.75(br s, 1H) |

TABLE 5-continued

| Example No. | Compound No. | R² | R⁵ | * | ¹H-NMR (DMSO-d₆) |
|---|---|---|---|---|---|
| 37 | A-37 | Bn | n-Bu—⟨phenyl⟩— | R | 0.92(t, J=7.4 Hz, 3H), 1.25–1.45(m, 2H), 1.70–1.50(m, 2H), 2.69(t, J=7.2 Hz, 2H), 2.75(m, 1H), 2.99(dd, J=4.8, 13.6 Hz, 1H), 3.95(m, 1H), 7.10–7.25(m, 5H), 7.44(d, J=8.4 Hz, 2H), 7.79(d, J=8.4 Hz, 2H), 8.03(d, J=8.0 Hz, 2H), 8.20(d, J=8.4 Hz, 2H), 8.60(br s, 1H) |

TABLE 6

| Example No. | Compound No. | R² | R⁵ | * | ¹H-NMR (DMSO-d₆) |
|---|---|---|---|---|---|
| 38 | A-38 | Bn | i-Pr—⟨phenyl⟩— | R | 1.26(d, J=6.6 Hz, 6H), 2.75(dd, J=9.6, 13.8 Hz, 1H), 2.99(dd, J=5.7, 13.8 Hz, 1H), 3.01(m, 1H), 3.98 (dt, J=5.7, 9.0 Hz, 1H), 7.12–7.22 (m, 5H), 7.50(d, J=7.8 Hz, 2H), 7.80 (d, J=8.7 Hz, 2H), 8.05(d, J=7.8 Hz, 2H), 8.21(d, J=8.7 Hz, 2H), 8.62(d, J=9.0 Hz, 1H), 12.82(br s, 1H) |
| 39 | A-39 | Bn | MeS—⟨phenyl⟩— | R | 2.56(s, 3H), 2.75(dd, J=9.3, 13.5 Hz, 1H), 2.99(dd, J=5.1, 13.5 Hz, 1H), 3.98(dt, J=5.7, 9.0 Hz, 1H), 7.09–7.21(m, 5H), 7.47(d, J=8.4 Hz, 2H), 7.79(d, J=8.1 Hz, 2H), 8.03 (d, J=8.4 Hz, 2H), 8.20(d, J=8.1 Hz, 2H), 8.60(d, J=9.0 Hz, 1H), 12.81(br s, 1H) |
| 40 | A-40 | Bn | F₃C—⟨phenyl⟩— | R | 2.75(dd, J=9.6 Hz, 1H), 3.00(dd, J=5.1, 13.8 Hz, 1H), 3.98(m, 1H), 7.10–7.25(m, 5H), 7.80(d, J=8.7 Hz, 2H), 8.01(d, J=8.1 Hz, 2H), 8.23(d, J=8.7 Hz, 2H), 8.34(d, J=8.4 Hz, 2H), 8.63(d, J=9.3 Hz, 1H), 12.84(br s, 1H) |
| 41 | A-41 | Bn | MeO—⟨phenyl⟩— | R | 2.74(dd, J=9.8, 13.6 Hz, 1H), 2.99 (dd, J=5.2, 13.6 Hz, 1H), 3.97(m, 1H), 7.05–7.30(m, 7H), 7.79(d, J=8.6 Hz, 2H), 8.06(d, J=8.8 Hz, 2H), 8.20 (d, J=8.8 Hz, 2H), 8.61(d, J=9.2 Hz, 1H), 12.84(br s, 1H) |
| 42 | A-42 | Bn | n-Pr—⟨phenyl⟩— | R | 0.92(t, J=7.2 Hz, 3H), 1.55–1.80(m, 2H), 2.67(t, J=7.6 Hz, 2H), 2.74(dd, J=9.6, 13.6 Hz, 1H), 2.99(dd, J=5.4 Hz, 13.6 Hz, 1H), 3.97(m, 1H), 7.05–7.30(m, 5H), 7.44(d, J=8.0 Hz, 2H), 7.79(d, J=8.4 Hz, 2H), 8.03(d, J=8.0 Hz, 2H), 8.20(d, J=8.8 Hz, 2H), 8.62 (d, J=9.2 Hz, 1H), 13.50 (m, 1H) |
| 43 | A-43 | Bn | n-Pr—⟨phenyl⟩— | S | 0.93(t, J=7.5 Hz, 3H), 1.58–1.73 (m, 2H), 2.67(t, J=8.1 Hz, 2H), 2.75 (dd, J=9.6, 13.5 Hz, 1H), 2.99 (dd, J=5.1, 13.5 Hz, 1H), 3.97(m, 1H), 7.08–7.22(m, 5H), 7.44(d, J=8.1 Hz, 2H), 7.79(d, J=8.1 Hz, 2H), 8.03(d, J=8.1 Hz, 2H), 8.20 (d, J=8.1 Hz, 2H), 8.58(d, J=7.8 Hz, 1H), 12.81(br s, 1H) |

TABLE 7

| Example No. | Compound No. | R² | R⁵ | * | ¹H-NMR (DMSO-d₆) |
|---|---|---|---|---|---|
| 44 | A-44 | Bn | pyrrolidin-1-yl-phenyl | R | 1.90–2.10(m, 4H), 2.74 (dd, J=9.8, 13.2 Hz, 1H), 2.99 (dd, J=5.2, 13.2 Hz, 1H), 3.10–3.50(m, 4H), 3.96 (m, 1H), 6.69(d, J=9.2 Hz, 2H), 7.05–7.25(m, 5H), 7.27(d, J=8.8 Hz, 2H), 7.90(d, J=8.8 Hz, 2H), 8.17 (d, J=8.8 Hz, 2H), 8.58(d, J=8.6 Hz, 1H), 12.70(br s, 1H) |
| 45 | A-45 | Bn | HOH₂C-phenyl | R | 2.75(dd, J=10.2, 13.5 Hz, 1H), 3.00 (dd, J=5.1, 13.5 Hz, 1H), 3.98(dt, J=5.4, 8.7 Hz, 1H), 4.62(s, 2H), 5.40 (br s, 1H), 7.08–7.24(m, 5H), 7.57(d, J=8.1 Hz, 2H), 7.80(d, J=8.1 Hz, 2H), 8.09(d, J=8.1 Hz, 2H), 8.21(d, J=8.1 Hz, 2H), 8.63(d, J=8.7 Hz, 1H), 12.84 (br s, 1H) |
| 46 | A-46 | Bn | HOH₂C-phenyl | S | 2.75(dd, J=9.6, 13.8 Hz, 1H), 2.99 (dd, J=5.1, 13.8 Hz, 1H), 3.97(m, 1H), 4.62(s, 2H), 5.40(br s, 1H), 7.09–7.22(m, 5H), 7.56(d, J=8.1 Hz, 2H), 7.79(d, J=8.4 Hz, 2H), 8.09(d, J=8.1 Hz, 2H), 8.21(d, J=8.4 Hz, 2H), 8.62(d, J=8.7 Hz, 1H), 12.85(br s, 1H) |
| 47 | A-47 | Bn | 3-Me-phenyl | R | 2.44(s, 3H), 2.75(dd, J=9.6, 13.8 Hz, 1H), 2.99(dd, J=5.4, 13.8 Hz, 1H), 3.98(dt, J=4.5, 9.0 Hz, 1H), 7.09–7.22 (m, 5H), 7.43–7.54(m, 2H), 7.77–7.83 (m, 2H), 7.90–7.96(m, 2H), 8.18–8.24 (m, 2H), 8.60(d, J=8.4 Hz, 1H), 12.80 (br s, 1H) |
| 48 | A-48 | Me | Me-phenyl | R | 1.21(d, J=7.0 Hz, 3H), 3.88(m, 1H), 7.70(d, J=8.6 Hz, 2H), 8.05(d, J=8.6 Hz, 2H), 8.13(d, J=8.8 Hz, 2H), 8.37 (d, J=8.6 Hz, 2H), 8.48(m, 1H), 12.70(m, 1H) |
| 49 | A-49 | Me | Me-phenyl | S | 1.21(d, J=7.2 Hz, 3H), 2.42(s, 3H), 3.87(m, 1H), 7.43(d, J=8.7 Hz, 2H), 8.01(d, J=8.7 Hz, 2H), 8.05(d, J=8.7 Hz, 2H), 8.36(d, J=8.7 Hz, 2H), 8.44 (br s, 1H), 12.73(br s, 1H) |
| 50 | A-50 | Me | i-Pr-phenyl | R | 1.21(d, J=7.2 Hz, 3H), 1.26(d, J=6.9 Hz, 6H), 3.00(m, 1H), 3.89(m, 1H), 7.49(d, J=8.1 Hz, 2H), 8.04(d, J=8.4 Hz, 2H), 8.05(d, J=8.1 Hz, 2H), 8.37 (d, J=8.4 Hz, 2H), 8.46(d, J=7.5 Hz, 1H), 12.63(br s, 1H) |

TABLE 8

| Example No. | Compound No. | R² | R⁵ | * | ¹H-NMR (DMSO-d₆) |
|---|---|---|---|---|---|
| 51 | A-51 | Me | Et-phenyl | R | 1.21(d, J=7.2 Hz, 3H), 1.24(t, J=7.2 Hz, 3H), 2.71(q, J=7.2 Hz, 2H), 3.88 (m, 1H), 7.46(d, J=7.8 Hz, 2H), 8.00–8.08(m, 4H), 8.37(d, J=7.8 Hz, 2H), 8.46(d, J=8.4 Hz, 1H), 12.66(br s, 1H) |
| 52 | A-52 | Me | F₃C-phenyl | R | 1.21(d, J=7.2 Hz, 3H), 3.88(m, 1H), 8.01(d, J=8.4 Hz, 2H), 8.06(d, J=8.8 Hz, 2H), 8.33(d, J=8.0 Hz, 2H), 8.40 (d, J=8.6 Hz, 2H), 8.05(m, 1H), 12.60 (m, 1H) |

TABLE 8-continued

| Example No. | Compound No. | R² | R⁵ | * | ¹H-NMR (DMSO-d₆) |
|---|---|---|---|---|---|
| 53 | A-53 | Me | MeO–C₆H₄– | R | 1.21(dd, J=7.4 Hz, 3H), 3.88(m, 1H), 3.86(s, 3H), 7.16(d, J=9.2 Hz, 2H), 8.04(d, J=8.4 Hz, 2H), 8.06(d, J=9.2 Hz, 2H), 8.36(d, J=8.4 Hz, 2H), 8.47 (d, J=8.4 Hz, 1H), 12.68(br s, 1H) |
| 54 | A-54 | Me | n-Pr–C₆H₄– | R | 0.92(t, J=7.2 Hz, 3H), 1.21(d, J=7.2 Hz, 3H), 1.50–1.75(m, 2H), 2.66(t, J=7.5 Hz, 2H), 3.88(m, 1H), 7.44(d, J=8.6 Hz, 2H), 8.03(d, J=8.4 Hz, 2H), 8.05(d, J=8.6 Hz, 2H), 8.37(d, J=8.4 Hz, 2H), 8.48(m, 1H), 12.70(br s, 1H) |
| 55 | A-55 | Me | n-Pr–C₆H₄– | S | 0.92(t, J=7.5 Hz, 3H), 1.20(d, J=7.2 Hz, 3H), 1.57–1.72(m, 2H), 2.66(t, J=7.2 Hz, 2H), 3.87(m, 1H), 7.44(d, J=8.4 Hz, 2H), 8.03(d, J=8.4 Hz, 2H), 8.05(d, J=8.7 Hz, 2H), 8.37(d, J=8.7 Hz, 2H), 8.47(m, 1H), 12.74(br s, 1H) |
| 56 | A-56 | Me | Br–C₆H₄– | R | 1.21(d, J=7.2 Hz, 3H), 3.88(m, 1H), 7.42–7.51(m, 2H), 8.02–8.08(m, 2H), 8.13–8.21(m, 2H), 8.34–8.40(m, 2H), 8.47(d, J=8.1 Hz, 1H), 12.67(br s, 1H) |
| 57 | A-57 | Me | MeS–C₆H₄– | R | 1.21(d, J=7.2 Hz, 3H), 2.56(s, 3H), 3.88(m, 1H), 7.47(d, J=9.0 Hz, 2H), 8.03(d, J=8.4 Hz, 2H), 8.05(d, J=8.4 Hz, 2H), 8.36(d, J=9.0 Hz, 2H), 8.48 (d, J=7.8 Hz, 1H), 12.68(br s, 1H) |
| 58 | A-58 | Me | O₂N–C₆H₄– | R | 1.21(d, J=7.5 Hz, 3H), 3.89(m, 1H), 8.04–8.09(m, 2H), 8.34–8.42(m, 4H), 8.43–8.54(m, 3H), 12.71(br s, 1H) |

TABLE 9

| Example No. | Compound No. | R² | R⁵ | * | ¹H-NMR(DMSO-d₆) |
|---|---|---|---|---|---|
| 59 | A-59 | Me | HO–C₆H₄– | R | 1.21(d, J=6.9 Hz, 3H), 3.88(m, 1H), 6.94–7.00(m, 2H), 7.91–7.98(m, 2H), 8.04(d, J=8.4 Hz, 2H), 8.35(d, J=8.4 Hz, 2H), 8.47(d, J=7.8 Hz, 1H), 10.21(br s, 1H), 12.67(br s, 1H) |
| 60 | A-60 | Me | HOH₂C–C₆H₄– | R | 1.21(d, J=7.2 Hz, 3H), 3.88(m, 1H), 4.62(s, 2H), 5.40(br s, 1H), 7.56(d, J=8.4 Hz, 2H), 8.05(d, J=8.4 Hz, 2H), 8.08(d, J=8.4 Hz, 2H), 8.37(d, J=8.4 Hz, 2H), 8.49(d, J=8.4 Hz, 1H), 12.70(br s, 1H) |
| 61 | A-61 | Me | HOOC–C₆H₄– | R | 1.21(d, J=7.2 Hz, 3H), 3.89(m, 1H), 8.06(d, J=8.4 Hz, 2H), 8.17 and 8.24(ABq, J=8.7 Hz, 4H), 8.39(d, J=8.4 Hz, 2H), 8.48(d, J=7.8 Hz, 1H), 12.70–12.30(br s, 2H) |
| 62 | A-62 | CH₂CH₂SMe | Cl–C₆H₄– | R | 1.69–1.96(m, 2H), 1.95(s, 3H), 2.26–2.50(m, 2H), 3.95(m, 1H), 7.70(d, J=9.0 Hz, 2H), 8.04(d, J=9.0 Hz, 2H), 8.13(d, J=8.7 Hz, 2H), 8.37(d, J=8.7 Hz, 2H), 8.50(d, J=7.2 Hz, 1H), 12.78(br s, 1H) |
| 63 | A-63 | CH₂CH₂SMe | Me–C₆H₄– | R | 1.69–1.97(m, 2H), 1.95(s, 3H), 2.26–2.51(m, 2H), 2.41(s, 3H), 3.94(m, 1H), 7.43(d, J=8.4 Hz, 2H), 8.02(t, 7.8 Hz, 4H), 8.36(d, J=8.4 Hz, 2H), 8.50(m, 1H), 12.78(br s, 1H) |

TABLE 9-continued

| Example No. | Compound No. | R² | R⁵ | * | ¹H-NMR(DMSO-d₆) |
|---|---|---|---|---|---|
| 64 | A-64 | 4-OH—Ph | Me—C₆H₄— | R | 2.42(s, 3H), 4.84(m, 1H), 6.60(d, J=8.7 Hz, 2H), 7.05(d, J=8.7 Hz, 2H), 7.43(d, J=8.1 Hz, 2H), 7.95(d, J=8.7 Hz, 2H), 8.01(d, J=8.1 Hz, 2H), 8.26(d, J=8.7 Hz, 2H), 8.86(m, 1H), 9.41(s, 1H), 12.88(br s, 1H) |
| 65 | A-65 | 4-OH—Ph | Et—C₆H₄— | R | 1.24(t, J=7.2 Hz, 3H), 2.72(q, J=7.2 Hz, 2H), 4.85(d, J=9.0 Hz, 1H), 6.61(d, J=8.4 Hz, 2H), 7.06(d, J=8.4 Hz, 2H), 7.46(d, J=8.1 Hz, 2H), 7.96(d, J=8.4 Hz, 2H), 8.03(d, J=8.4 Hz, 2H), 8.26(d, J=8.1 Hz, 2H), 8.86(d, J=9.0 Hz, 1H), 9.41(s, 1H), 12.84(m, 1H) |
| 66 | A-66 | H | Me—C₆H₄— | | 2.41(s, 3H), 3.69(s, 2H), 7.43(d, J=8.1 Hz, 2H), 8.01(d, J=8.1 Hz, 2H), 8.05(d, J=8.7 Hz, 2H), 8.37(d, J=8.7 Hz, 2H), 12.78(br s, 1H) |

TABLE 10

| Example No. | Compound No. | R² | R⁵ | * | ¹H-NMR(DMSO-d₆) |
|---|---|---|---|---|---|
| 67 | A-67 | H | Et—C₆H₄— | | 1.24(t, J=7.5 Hz, 3H), 2.72(q, J=7.5 Hz, 2H), 3.62–3.72(m, 2H), 7.46(d, J=8.7 Hz, 2H), 8.03(d, J=8.4 Hz, 2H), 8.06(d, J=8.4 Hz, 2H), 8.35(m, 1H), 8.37(d, J=8.7 Hz, 2H) |
| 68 | A-68 | H | Cl—C₆H₄— | | 3.77(d, J=4.2 Hz, 2H), 7.70(d, J=8.4 Hz, 2H), 8.06(d, J=8.4 Hz, 2H), 8.13(d, J=8.4 Hz, 2H), 8.38(d, J=8.4 Hz, 2H), 12.63(br s, 1H) |
| 69 | A-69 | H | C₆H₅— | | 3.70(d, J=5.4 Hz, 2H), 7.58–7.64(m, 3H), 8.06(d, J=9.0 Hz, 2H), 8.10–8.15(m, 4H), 8.38(d, J=9.0 Hz, 2H), 8.38(d, J=5.4 Hz, 1H), 12.74(br s, 1H) |
| 70 | A-70 | H | i-Pr—C₆H₄— | | 1.26(d, J=6.9 Hz, 6H), 3.00(m, 1H), 3.70(d, J=5.1 Hz, 2H), 7.46–7.51(m, 2H), 8.01–8.09(m, 4H), 8.33–8.41(m, 3H), 12.72(br s, 1H) |
| 71 | A-71 | H | n-Pr—C₆H₄— | | 0.92(t, J=7.0 Hz, 3H), 1.50–1.75(m, 2H), 2.66(t, J=7.5 Hz, 2H), 3.60–3.75(m, 2H), 7.44(d, J=8.2 Hz, 2H), 8.03(d, J=8.0 Hz, 2H), 8.06(d, J=8.2 Hz, 2H), 8.37(d, J=8.8 Hz, 2H), 8.40(m, 1H), 12.70(m, 1H) |
| 72 | A-72 | H | t-Bu—C₆H₄— | | 1.34(s, 9H), 3.70(d, J=5.4 Hz, 2H), 7.61–7.67(m, 2H), 8.02–8.09(m, 4H), 8.34–8.41(m, 3H), 12.73(br s, 1H) |
| 73 | A-73 | H | MeO—C₆H₄— | | 3.70(d, J=5.1 Hz, 2H), 3.86(s, 3H), 7.13–7.19(m, 2H), 8.02–8.08(m, 4H), 8.33–8.41(m, 3H), 12.70(br s, 1H) |
| 74 | A-74 | H | EtO—C₆H₄— | | 1.38(t, J=7.2 Hz, 3H), 3.71(d, J=5.7 Hz, 2H), 4.14(q, J=7.2 Hz, 2H), 7.11–7.18(m, 2H), 8.01–8.10(m, 4H), 8.33–8.41(m, 3H), 12.72(br s, 1H) |
| 75 | A-75 | H | F—C₆H₄— | | 3.69(s, 2H), 7.47(t, J=8.7 Hz, 2H), 8.06(d, J=8.7 Hz, 2H), 8.17(d, J=9.0 Hz, 2H), 8.18(d, J=9.3 Hz, 2H), 8.37(d, J=8.7 Hz, 2H), 12.75(br s, 1H) |

TABLE 10-continued

| Example No. | Compound No. | R² | R⁵ | * | ¹H-NMR(DMSO-d₆) |
|---|---|---|---|---|---|
| 76 | A-76 | Indol-3-yl methyl | Me—⟨C₆H₄⟩— | R | 2.42(s, 3H), 2.86(dd, J=9.3, 14.4 Hz, 1H), 3.08(dd, J=4.8, 14.4 Hz, 1H), 3.95(m, 1H), 6.82–6.92(m, 2H), 7.03–7.13(m, 2H), 7.31(m, 1H), 7.45(d, J=8.1 Hz, 2H), 7.61(d, J=8.7 Hz, 2H), 7.97(d, J=8.7 Hz, 2H), 8.03(d, J=8.1 Hz, 2H), 8.53(d, J=8.7 Hz, 1H), 10.73(s, 1H), 12.79(br s, 1H) |

TABLE 11

| Example No. | Compound No. | R² | R⁵ | * | ¹H-NMR(DMSO-d₆) |
|---|---|---|---|---|---|
| 77 | A-77 | Indol-3-yl methyl | Me—⟨C₆H₄⟩— | S | 2.42(s, 3H), 2.86(dd, J=9.3, 14.4 Hz, 1H), 3.08(dd, J=4.8, 14.4 Hz, 1H), 3.95(m, 1H), 6.82–6.92(m, 2H), 7.03–7.13(m, 2H), 7.31(m, 1H), 7.45(d, J=8.1 Hz, 2H), 7.61(d, J=8.7 Hz, 2H), 7.97(d, J=8.7 Hz, 2H), 8.03(d, J=8.1 Hz, 2H), 8.53(d, J=8.7 Hz, 1H), 10.73(s, 1H), 12.79(br s, 1H) |
| 78 | A-78 | Indol-3-yl methyl | F—⟨C₆H₄⟩— | R | 2.86(dd, J=9.6, 14.7 Hz, 1H), 3.09(dd, J=4.5, 14.7 Hz, 1H), 3.97(m, 1H), 6.83–6.92(m, 2H), 7.04–7.12(m, 2H), 7.30(m, 1H), 7.44–7.52(m, 2H), 7.62(d, J=9.0 Hz, 2H), 7.97(d, J=9.0 Hz, 2H), 8.16–8.23(m, 2H), 8.53(d, J=8.7 Hz, 1H), 10.72(s, 1H), 12.75(br, 1H) |
| 79 | A-79 | Indol-3-yl methyl | Cl—⟨C₆H₄⟩— | R | 2.86(dd, J=9.9, 14.1 Hz, 1H), 3.08(dd, J=4.2, 14.1 Hz, 1H), 3.95(m, 1H), 6.82–6.92(m, 2H), 7.02–7.12(m, 9H), 7.30(m, 1H), 7.61(d, J=8.4 Hz, 2H), 7.72(d, J=8.4 Hz, 2H), 7.97(d, J=8.4 Hz, 2H), 8.15(d, J=8.4 Hz, 2H), 8.55(m, 1H), 10.73(s, 1H) 12.80(br s, 1H) |
| 80 | A-80 | Indol-3-yl methyl | Et—⟨C₆H₄⟩— | R | 1.25(t, J=7.5 Hz, 3H), 2.73(J=7.5 Hz, 2H), 2.86(dd, J=9.6, 14.1 Hz, 1H), 3.09(dd, J=5.4, 14.1 Hz, 1H), 3.95(m, 1H), 6.82–6.90(m, 2H), 7.03–7.12(m, 2H), 7.30(m, 1H), 7.48(d, J=8.4 Hz, 2H), 7.62(d, J=8.4 Hz, 2H), 7.99(d, J=8.4 Hz, 2H), 8.05(d, J=8.4 Hz, 2H), 8.51(d, J=8.7 Hz, 1H), 10.72(s, 1H), 12.75(br, 1H) |
| 81 | A-81 | Indol-3-yl methyl | Et—⟨C₆H₄⟩— | S | 1.25(t, J=7.5 Hz, 3H), 2.73(q, J=7.5 Hz, 2H), 2.86(dd, J=9.3, 14.1 Hz, 1H), 3.09(dd, J=4.8, 14.1 Hz, 1H), 3.94(m, 1H), 6.82–6.92(m, 2H), 7.04–7.13(m, 2H), 7.31(m, 1H), 7.48(d, J=8.1 Hz, 2H), 7.62(d, J=8.4 Hz, 2H), 7.97(d, J=8.4 Hz, 2H), 8.06(d, J=8.1 Hz, 2H), 8.53(m, 1H), 10.73(s, 1H), 12.86(br s, 1H) |

TABLE 12

| Example No. | Compound No. | R² | R⁵ | * | ¹H-NMR(DMSO-d₆) |
|---|---|---|---|---|---|
| 82 | A-82 | Indol-3-yl methyl | n-Pr—⟨C₆H₄⟩— | S | 0.93(t, J=7.5 Hz, 3H), 1.59–1.74(m, 2H), 2.68(t, J=8.1 Hz, 2H), 2.86(dd, J=9.9, 14.7 Hz, 1H), 3.09(dd, J=5.1, 14.1 Hz, 1H), 3.95(m, 1H), 6.83–7.02(m, 2H), 7.04–7.13(m, 2H), 7.31(m, 1H), 7.46(d, J=7.8 Hz, 2H), 7.62(d, J=8.4 Hz, 2H), 7.97(d, J=8.4 Hz, 2H), 8.05(d, J=7.8 Hz, 2H), 8.51(d, J=7.2 Hz, 1H), 10.72(s, 1H), 12.77(br s, 1H) |

TABLE 12-continued

| Example No. | Compound No. | R² | R⁵ | * | ¹H-NMR(DMSO-d₆) |
|---|---|---|---|---|---|
| 83 | A-83 | Indol-3-yl methyl | n-Bu—C₆H₄— | R | 0.92(t, J=6.9 Hz, 3H), 1.28–1.41(m, 2H), 1.57–1.67(m, 2H), 2.69(t, J=7.5 Hz, 3H), 2.87(dd, J=9.0, 14.1 Hz, 1H), 3.09(dd, J=5.1, 14.7 Hz, 1H), 3.92(m, 1H), 6.86–6.89(m, 2H), 7.05(d, J=2.4 Hz, 1H), 7.10(m, 1H), 7.33(m, 1H), 7.45(d, J=8.4 Hz, 2H), 7.64(d, J=8.4 Hz, 2H), 7.98(d, J=8.7 Hz, 2H), 8.04(d, J=8.1 Hz, 2H), 8.40(br s, 1H), 10.70(s, 1H) |
| 84 | A-84 | i-Bu | Me—C₆H₄— | R | 0.75(d, J=6.3 Hz, 3H), 0.84(d, J=6.9 Hz, 3H), 1.35–1.52(m, 2H), 1.60(m, 1H), 2.41(s, 3H), 3.75(m, 1H), 7.43(d, J=8.1 Hz, 2H), 7.98–8.06(m, 4H), 8.33–8.39(m, 2H), 8.46(d, J=8.7 Hz, 1H), 12.64(br s, 1H) |
| 85 | A-85 | i-Bu | Me—C₆H₄— | S | 0.74(d, J=6.6 Hz, 3H), 0.84(d, J=6.6 Hz, 3H), 1.38–1.48(m, 2H), 1.60(m, 1H), 2.42(s, 3H), 3.75(m, 1H), 7.43(d, J=8.1 Hz, 2H), 8.01(d, J=8.4 Hz, 2H), 8.03(d, J=8.4 Hz, 2H), 8.36(d, J=8.1 Hz, 2H), 8.45(m, 1H), 12.60(br, 1H) |
| 86 | A-86 | i-Bu | F—C₆H₄— | R | 0.75(d, J=6.3 Hz, 3H), 0.84(d, J=6.6 Hz, 3H), 1.35–1.52(m, 2H), 1.60(m, 1H), 3.76(m, 1H), 7.42–7.51(m, 2H), 8.01–8.07(m, 2H), 8.14–8.22(m, 2H), 8.34–8.39(m, 2H), 8.47(d, J=8.4 Hz, 1H), 12.63(br s, 1H) |
| 87 | A-87 | i-Bu | Cl—C₆H₄— | R | 0.75(d, J=6.6 Hz, 3H), 0.84(d, J=6.6 Hz, 3H), 1.35–1.52(m, 2H), 1.60(m, 1H), 3.76(m, 1H), 7.67–7.73(m, 2H), 8.01–8.06(m, 2H), 8.10–8.16(m, 2H), 8.34–8.40(m, 2H), 8.47(d, J=7.8 Hz, 1H), 12.63(br s, 1H) |

TABLE 13

| Example No. | Compound No. | R² | R⁵ | * | ¹H-NMR(DMSO-d₆) |
|---|---|---|---|---|---|
| 88 | A-88 | i-Bu | n-Pr—C₆H₄— | S | 0.75(d, J=6.6 Hz, 3H), 0.84(d, J=6.6 Hz, 3H), 0.92(t, J=6.9 Hz, 3H), 1.38–1.48(m, 2H), 1.60(m, 1H), 1.65(q, J=7.5 Hz, 2H), 2.67(t, J=7.5 Hz, 2H), 3.75(m, 1H), 7.44(d, J=8.1 Hz, 2H), 8.03(d, J=8.1 Hz, 2H), 8.36(d, J=8.1 Hz, 2H), 8.45(m, 1H), 12.61(br, 1H) |
| 89 | A-89 | 4-OH—Bn | F—C₆H₄— | R | 2.62(dd, J=9.3, 13.8 Hz, 1H), 2.87(d, J=5.1, 13.8 Hz, 1H), 3.88(m, 1H), 6.52(d, J=8.1 Hz, 2H), 6.91(d, J=8.1 Hz, 2H), 7.47(t, J=8.7 Hz, 2H), 7.77(d, J=8.4 Hz, 2H), 8.14–8.25(m, 4H), 8.54(d, J=8.7 Hz, 1H), 9.12(br s, 1H), 12.76(br s, 1H) |
| 90 | A-90 | 4-OH—Bn | C₆H₅— | R | 2.62(dd, J=9.6, 13.5 Hz, 1H), 2.87(dd, J=5.4, 13.5 Hz, 1H), 3.86(br s, 1H), 6.52(d, J=8.4 Hz, 2H), 6.91(d, J=8.4 Hz, 2H), 7.54–7.71(m, 3H), 7.78(d, J=8.7 Hz, 2H), 8.11–8.15(m, 2H), 8.22(d, J=8.7 Hz, 2H), 8.53(br s, 1H), 9.12(s, 1H), 12.78(br s, 1H) |
| 91 | A-91 | i-Pr | pyridin-4-yl | R | 0.75–0.85(m, 6H), 1.99(m, 1H), 3.61(m, 1H), 7.99–8.00(m, 4H), 8.38–8.50(m, 3H), 8.82(d, J=6.2 Hz, 2H), 12.45(m, 1H) |
| 92 | A-92 | i-Pr | thiophen-3-yl | R | 0.82(d, J=6.9 Hz, 3H), 0.85(d, J=6.6 Hz, 3H), 1.98(m, 1H), 3.61(dd, J=6.0, 9.0 Hz, 1H), 7.67(dd, J=1.2, 5.1 Hz, 1H), 7.82(dd, J=3.0, 5.1 Hz, 1H), 8.01–8.07(m, 2H), 8.30–8.37(m, 3H), 8.40(dd, J=1.2, 3.0 Hz, 1H), 12.63(br s, 1H) |

TABLE 13-continued

| Example No. | Compound No. | R² | R⁵ | * | ¹H-NMR(DMSO-d₆) |
|---|---|---|---|---|---|
| 93 | A-93 | i-Pr | Me—[thiophene]— | R | 0.82(d, J=6.9 Hz, 3H), 0.85(d, J=7.2 Hz, 3H), 1.98(m, 1H), 2.56(s, 3H), 3.61(dd, J=6.6, 7.8 Hz, 1H), 7.02(m, 1H), 7.72(dd, J=1.5, 3.6 Hz, 1H), 8.00–8.06(m, 2H), 8.29–8.35(m, 2H), 8.37(d, J=7.8 Hz, 1H), 12.65(br s, 1H) |
| 94 | A-94 | i-Pr | Me—[thiophene]— | S | 0.81(d, J=6.6 Hz, 3H), 0.85(d, J=6.6 Hz, 3H), 1.97(m, 1H), 2.56(s, 3H), 3.60(dd, J=6.3, 8.1 Hz, 1H), 7.01(d, J=3.6 Hz, 1H), 7.72(d, J=3.6 Hz, 1H), 8.02(d, J=8.7 Hz, 2H), 8.32(d, J=8.7 Hz, 2H), 8.35(m, 1H), 12.66(br, 1H) |

TABLE 14

| Example No. | Compound No. | R² | R⁵ | * | ¹H-NMR(DMSO-d₆) |
|---|---|---|---|---|---|
| 95 | A-95 | i-Pr | [furan] | R | 2.74(dd, J=9.6, 13.5 Hz, 1H), 2.99(dd, J=5.1, 13.5 Hz, 1H), 3.97(dt, J=5.1, 9.0 Hz, 1H), 6.81(dd, J=1.8, 3.3 Hz, 1H), 7.08–7.21(m, 5H), 7.38(dd, J=0.6, 3.3 Hz, 1H), 7.75–7.82(m, 2H), 8.06(dd, J=0.6, 1.8 Hz, 1H), 8.15–8.21(m, 2H), 8.61(d, J=9.0 Hz, 1H), 12.82(br s, 1H) |
| 96 | A-96 | i-Pr | Cl—[thiophene]— | R | 0.81(d, J=6.6 Hz, 3H), 0.85(d, J=6.9 Hz, 3H), 1.98(m, 1H), 3.60(t, J=6.6 Hz, 1H), 7.37(d, J=3.9 Hz, 1H), 7.80(d, J=3.9 Hz, 1H), 8.01–8.06(m, 2H), 8.29–8.39(m, 3H), 12.63(br s, 1H) |
| 97 | A-97 | i-Pr | Cl—[thiophene]— | S | 0.81(d, J=6.9 Hz, 3H), 0.84(d, J=6.9 Hz, 3H), 1.98(m, 1H), 2.09(s, 3H), 3.60(dd, J=6.0, 8.4 Hz, 1H), 7.37(d, J=4.2 Hz, 1H), 7.80(d, J=4.2 Hz, 1H), 8.03(d, J=8.4 Hz, 2H), 8.32(d, J=8.4 Hz, 2H), 8.35(m, 1H) |
| 98 | A-98 | Bn | [thiophene] | R | 2.74(dd, J=9.6, 14.1 Hz, 1H), 2.99(dd, J=5.4, 14.1 Hz, 1H), 3.97(dt, J=4.8, 9.0 Hz, 1H), 7.09–7.21(m, 5H), 7.31(dd, J=3.6, 4.8 Hz, 1H), 7.79(d, J=8.1 Hz, 2H), 7.93(d, J=3.6 Hz, 1H), 7.95(d, J=4.8 Hz, 1H), 8.19(d, J=8.1 Hz, 2H), 8.62(d, J=9.0 Hz, 1H), 12.84(br s, 1H) |
| 99 | A-99 | Bn | [pyridine] | R | 2.74(dd, J=9.2, 13.6 Hz, 1H), 3.00(dd, J=5.0, 13.6 Hz 1H), 4.00(m, 1H), 7.10–7.30(m, 5H), 7.80(d, J=8.4 Hz, 2H), 8.05(d, J=5.8 Hz, 2H), 8.23(d, J=8.4 Hz, 2H), 8.62(d, J=9.2 Hz, 1H), 8.87(d, J=5.2 Hz, 2H), 12.80(m, 1H) |
| 100 | A-100 | Bn | Me—[thiophene]— | R | 2.56(s, 3H), 2.74(dd, J=9.6, 13.5 Hz, 1H), 2.99(dd, J=4.8, 13.5 Hz, 1H), 3.97(dt, J=4.8, 9.0 Hz, 1H), 7.02(dd, J=1.2, 3.6 Hz, 1H), 7.08–7.21(m, 5H), 7.72(d, J=3.6 Hz, 1H), 7.75–7.81(m, 2H), 8.13–8.20(m, 2H), 8.61(d, J=9.0 Hz, 1H), 12.83(br s, 1H) |
| 101 | A-101 | Bn | Cl—[thiophene]— | R | 2.74(dd, J=9.3, 13.5 Hz, 1H), 2.99(dd, J=4.8, 13.5 Hz, 1H), 3.97(dt, J=5.1, 9.0 Hz, 1H), 7.07–7.21(m, 5H), 7.37(d, J=3.9 Hz, 1H), 7.72(d, J=3.6 Hz, 1H), 7.75–7.82(m, 2H), 7.79(d, J=3.9 Hz, 1H), 8.14–8.20(m, 2H), 8.61(d, J=9.0 Hz, 1H), 12.80(br s, 1H) |

TABLE 15

| Example No. | Compound No. | $R^2$ | $R^5$ | * | $^1$H-NMR(DMSO-$d_6$) |
|---|---|---|---|---|---|
| 102 | A-102 | Me | 2-thienyl | R | 1.21(d, J=7.2 Hz, 3H), 3.88(m, 1H), 7.32(dd, J=3.6, 4.8 Hz, 1H), 7.92(dd, J=1.2, 3.6 Hz, 1H), 7.95(dd, J=1.2, 4.8 Hz, 1H), 8.05(d, J=8.4 Hz, 2H), 8.35(d, J=8.4 Hz, 2H), 8.48(d, J=8.1 Hz, 1H), 12.68(br s, 1H) |
| 103 | A-103 | Me | 2-thienyl | S | 1.21(d, J=7.2 Hz, 3H), 3.88(m, 1H), 7.32(dd, J=3.6, 5.1 Hz, 1H), 7.91(dd, J=1.2, 3.6 Hz, 1H), 7.95(dd, J=1.2, 5.1 Hz, 1H), 8.01–8.07(m, 2H), 8.32–8.38(m, 2H), 8.48(d, J=7.2 Hz, 1H), 12.70(br s, 1H) |
| 104 | A-104 | Me | 3-thienyl | R | 1.21(d, J=7.5 Hz, 3H), 3.88(m, 1H), 7.67(dd, J=1.2, 4.8 Hz, 1H), 7.83(dd, J=3.3, 4.8 Hz, 1H), 8.02–8.08(m, 2H), 8.32–8.38(m, 2H), 8.40(dd, J=1.2, 3.3 Hz, 1H), 8.46(d, J=7.8 Hz, 1H), 12.67(br s, 1H) |
| 105 | A-105 | Me | 5-methyl-2-thienyl | R | 1.21(d, J=7.5 Hz, 3H), 2.56(s, 3H), 3.88(m, 1H), 7.02(m, 1H), 7.72(m, 1H), 8.01–8.07(m, 2H), 8.30–8.37(m, 2H), 8.49(d, J=8.1 Hz, 1H), 12.71(br s, 1H) |
| 106 | A-106 | Me | 2-furyl | R | 1.20(d, J=7.2 Hz, 3H), 3.88(m, 1H), 6.81(dd, J=1.5, 3.3 Hz, 1H), 7.37(dd, J=0.9, 3.3 Hz, 1H), 8.02–8.07(m, 3H), 8.31–8.38(m, 2H), 8.48(d, J=7.2 Hz, 1H), 12.70(br s, 1H) |
| 107 | A-107 | Me | 5-chloro-2-thienyl | R | 1.20(d, J=7.5 Hz, 3H), 3.87(m, 1H), 7.36(d, J=3.9 Hz, 1H), 7.80(d, J=3.9 Hz, 1H), 8.01–8.07(m, 2H), 8.30–8.36(m, 2H), 8.46(d, J=8.4 Hz, 1H), 12.67(br s, 1H) |
| 108 | A-108 | Indol-3-yl methyl | 2-thienyl | R | 2.86(dd, J=9.6, 14.4 Hz, 1H), 3.09(dd, J=4.8, 14.4 Hz, 1H), 3.95(dt, J=4.2, 9.0 Hz, 1H), 6.85–6.91(m, 2H), 7.05(d, J=2.1 Hz, 1H), 7.10(m, 1H), 7.28–7.36(m, 2H), 7.62(d, J=8.1 Hz, 2H), 7.92–7.98(m, 4H), 8.52(d, J=9.0 Hz, 1H), 10.72(s, 1H), 12.77(br s, 1H) |

Test Example 1

Isolation and Purification of MMPs

MMP-2 was purchased from Calbiochem-Novabiochem International, Inc.

MMP-9 was purchased from Calbiochem-Novabiochem International, Inc.

The DNA fragment corresponding to MMP-8 Catalytic domain ($^{99}$Phe~$^{262}$Gly) was amplified by PCR with specific primers and Human Bone Marrow cDNA which was on the market. The DNA fragment was cloned into an *E. coli* expression vector, pTrc99A containing the His-tag sequence and Enterokinase digestion site. The MMP-8 Catalytic domain expression was induced by the addition of IPTG (Isopropyl-β-D-thiogalactopyranoside), and the cell pellet containing MMP-8 Catalytic domain was obtained. (We used a slightly modified method described in Thau F. Ho M. Walid Qoronfleh, Robert C. Wail, Trica A. Pulvino, Karen J. Vavra, Joe Falvo, Tracey M. Banks, Patricia G. Brake and Richard B. Ciccarelli: Gene expression, purification and characterization of recombinant human neutrophil collagenase. Gene 146, (1994) 297–301). Isolation of MMP-8 from the cell pellet was used by general techniques. After the cell pellet was dissolved in 6M urea, the solution was loaded onto a metal-chelating matrix. Subsequently, dialysis was used to remove urea and refold of MMP=8. And then active MMP-8 was obtained.

Test Example 2

Assay for Inhibitory Activities on MMPs

The enzymatic activity on MMPs was analyzed by the method described in "C. Graham Knight, Frances Willenbrock and Gillian Murphy: A novel coumarin-labelled peptide for sensitive continuous assays of the matrix metalloproteinases: FEBS LETT., 296, (1992), 263–266". The substrate (MOCAc-Pro-Leu-Gly-Leu-A$_2$Pr(DNP)-Ala-Arg-NH$_2$) was purchased from Peptide Institute, Inc., Osaka, Japan.

The measurement of the inhibitory activities (IC$_{50}$) was carried out by the following four methods;

A) Reaction with substrate, enzyme (MMPs) and inhibitor

B) Reaction with substrate and inhibitor, without enzyme

C) Reaction with substrate and enzyme (MMPs), without inhibitor

D) Reaction with substrate only

IC$_{50}$ values were calculated by using the following formula and each fluorescence values of above four methods (A to D).

$$\% \text{ inhibition} = \{1-(A-B)/(C-D)\} \times 100$$

$IC_{50}$ means the concentration required to inhibit 50% of the enzyme activity.

The results are shown in Table 16.

TABLE 16

| Compound No. | MMP-2 (nM) | MMP-8 (nM) | MMP-9 (nM) |
|---|---|---|---|
| A-1 | 30 | >1000 | 470 |
| A-2 | 53 | >1000 | >1000 |
| A-3 | 15 | 775 | 384 |
| A-4 | 26 | >1000 | 190 |
| A-5 | 30 | 610 | >1000 |
| A-6 | 50 | >1000 | >1000 |
| A-7 | 8 | >1000 | 78 |
| A-8 | 51 | >1000 | 479 |
| A-9 | 18 | >1000 | 566 |

TABLE 16-continued

| Compound No. | MMP-2 (nM) | MMP-8 (nM) | MMP-9 (nM) |
|---|---|---|---|
| A-10 | 65 | >1000 | >1000 |
| A-93 | 6 | 88 | 47 |

Test Example 3

Method for Evaluation of Antitumor Efficacy using Artificial Lung Metasasis of Lewis Mouse Lung Carcinoma Lewis mouse lung carcinoma cells ($4 \times 10^5$ cells) were inoculated into the tail vein of BDF1 mice. Test compounds were suspended in the vehicle (0.5% methylcellulose solution) and were orally administered to the mice total five times (−4, 1, 24, 48 and 72 h after tumor inoculation). The doses of the compounds were 20 and 200 mg/kg or 2 and 20 mg/kg. At 14 day after tumor inoculation, tumor nodules formed in the lung of the treated mice were counted and the antitumor efficacy was evaluated. The following compound (B-1) was used as reference. The results were summarized in Table 17.

TABLE 17

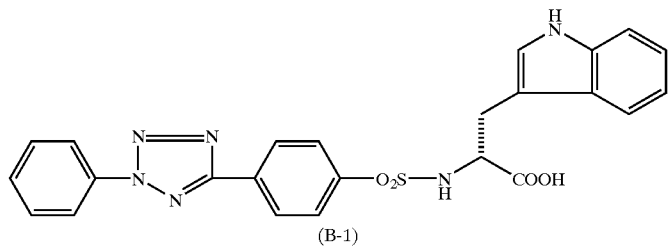

(B-1)

| Example No. | Compound No. | Amount (mg/kg) | Number of colonies (Mean ± SD) | Inhibition (%) |
|---|---|---|---|---|
| 3-1 | Control | — | 42.8 ± 12.7 | 0 |
| | B-1 | 20 | 26.5 ± 19.5 | 38 |
| | B-1 | 200 | 23.0 ± 7.6* | 46 |
| | A-1 | 20 | 20.2 ± 13.3* | 53 |
| | A-1 | 200 | 13.3 ± 11.8** | 69 |
| | A-4 | 20 | 19.2 ± 9.4** | 55 |
| | A-4 | 200 | 23.3 ± 12.8* | 46 |
| | A-7 | 20 | 18.8 ± 6.9** | 56 |
| | A-7 | 200 | 21.7 ± 9.6** | 49 |
| | A-8 | 20 | 18.8 ± 11.4** | 56 |
| | A-8 | 200 | 15.7 ± 5.5** | 63 |
| | A-10 | 20 | 24.5 ± 7.8* | 43 |
| | A-10 | 200 | 25.2 ± 17.0 | 41 |
| 3-2 | Control | — | 55.2 ± 13.6 | 0 |
| | B-1 | 20 | 34.8 ± 14.5* | 37 |
| | B-1 | 200 | 38.3 ± 20.7 | 31 |
| | A-2 | 20 | 34.8 ± 19.5 | 37 |
| | A-2 | 200 | 30.2 ± 13.9* | 45 |
| | A-5 | 20 | 41.8 ± 22.5 | 24 |
| | A-5 | 200 | 34.8 ± 12.1* | 37 |
| | A-6 | 20 | 40.8 ± 13.5 | 26 |
| | A-6 | 200 | 24.0 ± 9.7** | 57 |
| | A-9 | 20 | 38.7 ± 5.8* | 30 |
| | A-9 | 200 | 27.0 ± 9.7** | 51 |
| 3-3 | Control | — | 61.8 ± 7.9 | 0 |
| | B-1 | 2 | 53.5 ± 18.5 | 14 |
| | B-1 | 20 | 37.5 ± 13.0** | 39 |
| | A-93 | 2 | 36.3 ± 9.2** | 41 |
| | A-93 | 20 | 30.8 ± 10.8** | 50 |

Table 16 shows that tested compounds selectively inhibit MMP-2.

Table 17 shows that tested compounds exhibit a significant inhibitory effect against metastasis and increase of cancer cells.

Formulation Example

Formulation Example 1

Granules are prepared using the following ingredients.

| Ingredients | | |
|---|---|---|
| | The compound represented by the formula (I) | 10 mg |
| | Lactose | 700 mg |
| | Corn starch | 274 mg |
| | HPC-L | 16 mg |
| | | 1000 mg |

The compound represented by the formula (I) and lactose are made pass through a 60 mesh sieve. Corn starch is made pass through a 120 mesh sieve. They are mixed by a twin shell blender. An aqueous solution of HPC-L (low mucosity hydroxypropylcellulose) is added to the mixture and the resulting mixture is kneaded, granulated (by the extrusion with pore size 0.5 to 1 mm mesh), and dried. The dried granules thus obtained are sieved by a swing sieve (12/60 mesh) to yield the granules.

Formulation 2

Powders for filling capsules are prepared using the following ingredients.

| Ingredients | | |
|---|---|---|
| | The compound represented by the formula (I) | 10 mg |
| | Lactose | 79 mg |
| | Corn starch | 10 mg |
| | Magnesium stearate | 1 mg |
| | | 100 mg |

The compound represented by the formula (I) and lactose are made pass through a 60 mesh sieve. Corn starch is made pass through a 120 mesh sieve. These ingredients and magnesium stearate are mixed by a twin shell blender. 100 mg of the 10-fold trituration is filled into a No. 5 hard gelatin capsule.

Formulation 3

Granules for filling capsules are prepared using the following ingredients.

| Ingredients | | |
|---|---|---|
| | The compound represented by the formula (I) | 15 mg |
| | Lactose | 90 mg |
| | Corn starch | 42 mg |
| | HPC-L | 3 mg |
| | | 150 mg |

The compound represented by the formula (I) and lactose are made pass through a 60 mesh sieve. Corn starch is made pass through a 120 mesh sieve. After mixing them, an aqueous solution of HPC-L is added to the mixture and the resulting mixture is kneaded, granulated, and dried. After the dried granules are lubricated, 150 mg of that are filled into a No. 4 hard gelatin capsule.

Formulation 4

Tablets are prepared using the following ingredients.

| Ingredients | | |
|---|---|---|
| | The compound represented by the formula (I) | 10 mg |
| | Lactose | 90 mg |
| | Microcrystal cellulose | 30 mg |
| | CMC-Na | 15 mg |
| | Magnesium stearate | 5 mg |
| | | 150 mg |

The compound represented by the formula (I), lactose, microcrystal cellulose, and CMC-Na (carboxymethylcellulose sodium salt) are made pass through a 60 mesh sieve and then mixed. The resulting mixture is mixed with magnesium stearate to obtain the mixed powder for the tablet formulation. The mixed powder is compressed to yield tablets of 150 mg.

INDUSTRIAL APPLICABILITY

The sulfonamide derivatives having oxadiazole rings of the present invention have an inhibitory activity against metalloprotease, especially MMP-2 and are useful as treating or preventing agents of cancer.

What is claimed is:

1. A pharmaceutical composition for inhibiting matrix metalloproteinase containing a compound of the general formula (I), a prodrug, a pharmaceutically acceptable salt, or a solvate thereof as an active ingredient:

$$R^5 \diagup\!\!\!\diagdown R^4-SO_2-N(R^3)-CH(R^2)-COR^1 \quad (I)$$
(with oxadiazole ring)

wherein
- $R^1$ is hydroxy;
- $R^2$ is hydrogen, optionally substituted lower alkyl, optionally substituted aryl, or optionally substituted aralkyl;
- $R^3$ is hydrogen, optionally substituted lower alkyl, optionally substituted aryl, or optionally substituted aralkyl;
- $R^4$ is unsubstituted and
- $R^5$ is optionally substituted thienyl.

2. A compound of the formula (I'):

$$R^{10} \diagup\!\!\!\diagdown R^9-SO_2-N(R^8)-CH(R^7)-COR^6 \quad (I')$$

wherein
- $R^6$ is hydroxy;
- $R^7$ is hydrogen, methyl, isopropyl, isobutyl, benzyl, or indol-3-ylmethyl;
- $R^8$ is hydrogen or optionally substituted lower alkyl;
- $R^9$ is unsubstituted phenylene;
- $R^{10}$ is optionally substituted thienyl;
- a prodrug, or a pharmaceutically acceptable salt, or a solvate thereof.

3. A compound of the following formula:

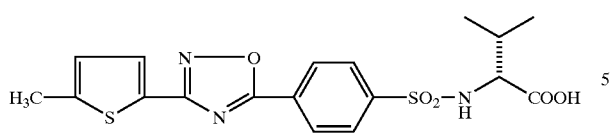

a prodrug, or a pharmaceutically acceptable salt, or a solvate thereof.

4. A pharmaceutical composition which contains as an active ingredient a compound as described in claim 2 or 3.

5. A method for inhibiting matrix metalloproteinase by administering to a mammal, a therapeutically effective amount of the compound as described claims 1, 2 or 3.

6. The method of claim 5 wherein the mammal is a human.

7. A pharmaceutical composition for treating lung cancer containing a compound of the general formula (I), a prodrug, a pharmaceutically acceptable salt, or a solvate thereof as an active ingredient:

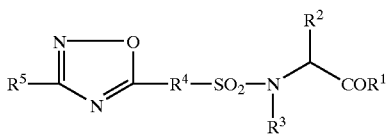

wherein
$R^1$ is hydroxy;
$R^2$ is hydrogen, optionally substituted lower alkyl, optionally substituted aryl, or optionally substituted aralkyl;
$R^3$ is hydrogen, optionally substituted lower alkyl, optionally substituted aryl, or optionally substituted aralkyl;
$R^4$ is unsubstituted phenylene; and
$R^5$ is optionally substituted thienyl.

8. A method for treating lung cancer by administering to a mammal a therapeutically effective amount of the compound as described in claims 1, 2, or 3.

* * * * *

UNITED STATES PATENT AND TRADEMARK OFFICE
CERTIFICATE OF CORRECTION

PATENT NO.      : 6,720,343 B2
DATED           : April 13, 2004
INVENTOR(S)     : Takayuki Yoshioka et al.

It is certified that error appears in the above-identified patent and that said Letters Patent is hereby corrected as shown below:

<u>Title page,</u>
Item [30], Foreign Application Priority Data, insert as follows:
-- April 21, 2000  (JP) ................. 2000-120234 --

<u>Column 42,</u>
Line 46, change "$R^4$ is unsubstituted and" to -- $R^4$ is unsubstituted phenylene and --.

Signed and Sealed this

Twelfth Day of July, 2005

JON W. DUDAS
*Director of the United States Patent and Trademark Office*